US012662480B2

(12) United States Patent
Edmunds

(10) Patent No.: US 12,662,480 B2
(45) Date of Patent: Jun. 23, 2026

(54) MICROBIOCIDAL DERIVATIVES

(71) Applicant: SYNGENTA CROP PROTECTION AG, Basel (CH)

(72) Inventor: Andrew Edmunds, Stein (CH)

(73) Assignee: SYNGENTA CROP PROTECTION AG, Basel (CH)

( * ) Notice: Subject to any disclaimer, the term of this patent is extended or adjusted under 35 U.S.C. 154(b) by 556 days.

(21) Appl. No.: 18/000,219

(22) PCT Filed: May 27, 2021

(86) PCT No.: PCT/EP2021/064263
§ 371 (c)(1),
(2) Date: Nov. 29, 2022

(87) PCT Pub. No.: WO2021/244952
PCT Pub. Date: Dec. 9, 2021

(65) Prior Publication Data

US 2023/0192678 A1 Jun. 22, 2023

(30) Foreign Application Priority Data

Jun. 3, 2020 (EP) .................................... 20178038

(51) Int. Cl.

| | |
|---|---|
| ***C07D 417/14*** | (2006.01) |
| ***A01N 43/78*** | (2006.01) |
| ***A01P 3/00*** | (2006.01) |
| ***C07D 417/12*** | (2006.01) |

(52) U.S. Cl.
CPC ........... *C07D 417/14* (2013.01); *A01N 43/78* (2013.01); *A01P 3/00* (2021.08); *C07D 417/12* (2013.01)

(58) Field of Classification Search
CPC .... C07D 417/14; C07D 417/12; A01N 43/78; A01P 3/00
See application file for complete search history.

(56) References Cited

FOREIGN PATENT DOCUMENTS

| | | | | |
|---|---|---|---|---|
| IL | 87643 A | 5/1994 | | |
| WO | 2010012793 A1 | 2/2010 | | |
| WO | 2017207362 A1 | 12/2017 | | |
| WO | 2019105933 A1 | 6/2019 | | |
| WO | 2020109511 A1 | 6/2020 | | |
| WO | WO-2020193618 A1 * | 10/2020 | ............ | A01N 43/80 |

OTHER PUBLICATIONS

Aromatic Bioisoteres, Bioisosteric Replacements, Cambrige MedChem Consulting, Sep. 1, 2016 or earlier by Wayback Machine Archive, Retrieved online on Sep. 15, 2025, Weblink: <www.cambridgemedchemconsulting.com/resources/bioisoteres/aromatic_bioisosteres.html> (Year: 2016).*
EPO; App. No. EP20178038.4; Extended European Search Report dated Oct. 9, 2020; pp. 1-6.
WIPO; App. No. PCT/EP2021/064263; International Search Report and Written Opinion dated Sep. 16, 2021; pp. 1-14.

* cited by examiner

*Primary Examiner* — Sue X Liu
*Assistant Examiner* — Dongxiu Zhang
(74) *Attorney, Agent, or Firm* — BakerHostetler; Toni-Junell Herbert

(57) ABSTRACT

Compounds of the formula (I) 5 R 8 R 1 R 7 R 6 R 5 R 4 R 3 R 2 N O N A F N S O (I) wherein the substituents are as defined in claim 1, useful as pesticides, and especially fungicides.

(I)

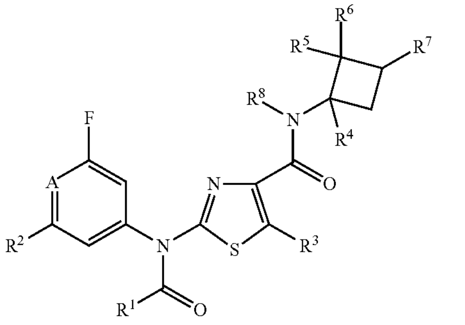

12 Claims, No Drawings

MICROBIOCIDAL DERIVATIVES

CROSS-REFERENCE TO RELATED APPLICATIONS

This application is a 371 National Stage Application of International Application No. PCT/EP2021/064263, filed May 27, 2021, which claims priority to EP 20178038.4, filed Jun. 3, 2020, the entire contents of which are incorporated by reference herein.

The present invention relates to microbiocidal thiazole derivatives, e.g., as active ingredients, which have microbiocidal activity, in particular fungicidal activity. The invention also relates to the preparation of these thiazole derivatives, to agrochemical compositions which comprise at least one of the thiazole derivatives and to uses of the thiazole derivatives or compositions thereof in agriculture or horticulture for controlling or preventing the infestation of plants, harvested food crops, seeds or non-living materials by phytopathogenic microorganisms, preferably fungi.

WO 2010/012793 and WO 2017/207362 describe thiazole derivatives as pesticidal agents.

According to the present invention, there is provided a compound of formula (I):

(I)

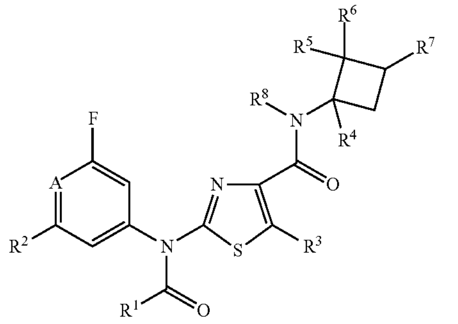

wherein

A is C—H or N;

$R^1$ is $C_1$-$C_4$alkoxy$C_1$-$C_2$alkyl, $C_1$-$C_6$alkylsulfanyl$C_1$-$C_6$alkyl, $C_1$-$C_6$alkylsulfinyl$C_1$-$C_6$alkyl, $C_1$-$C_6$alkylsulfonyl$C_1$-$C_6$alkyl, or heterocyclyl, wherein the heterocyclyl moiety is a 4-, 5- or 6-membered non-aromatic monocyclic ring comprising 1, 2 or 3 heteroatoms individually selected from nitrogen, oxygen and sulfur;

$R^2$ is hydrogen or halogen;

$R^3$ is $C_1$-$C_8$alkyl;

$R^4$, $R^5$, $R^6$ are each independently hydrogen or $C_1$-$C_4$alkyl;

$R^7$ is hydrogen, $C_1$-$C_4$alkyl, $C_1$-$C_6$alkoxycarbonyl$C_1$-$C_4$alkyl, $C_1$-$C_6$alkoxycarbonyl, or $C_1$-$C_6$alkoxy;

$R^8$ is hydrogen, $C_1$-$C_6$alkoxy$C_1$-$C_6$alkycarbonyl, $C_1$-$C_6$alkylsulfanyl$C_1$-$C_6$alkylcarbonyl, $C_1$-$C_6$alkylsulfinyl$C_1$-$C_6$alkycarbonyl, $C_1$-$C_6$alkylsulfonyl$C_1$-$C_6$alkycarbonyl, or heterocyclylcarbonyl, wherein the heterocyclyl moiety is a 4-, 5- or 6-membered non-aromatic monocyclic ring comprising 1, 2 or 3 heteroatoms individually selected from nitrogen, oxygen and sulfur;

or a salt or an N-oxide thereof.

According to a second aspect of the invention, there is provided an agrochemical composition comprising a fungicidally effective amount of a compound of formula (I) according to the present invention. Such an agricultural composition may further comprise at least one additional active ingredient and/or an agrochemically-acceptable diluent or carrier.

According to a third aspect of the invention, there is provided a method of controlling or preventing infestation of useful plants by phytopathogenic microorganisms, wherein a fungicidally effective amount of a compound of formula (I), or a composition comprising this compound as active ingredient, is applied to the plants, to parts thereof or the locus thereof.

According to a fourth aspect of the invention, there is provided the use of a compound of formula (I) as a fungicide. According to this particular aspect of the invention, the use may or may not include methods for the treatment of the human or animal body by surgery or therapy.

As used herein, the term "halogen" refers to fluorine (fluoro), chlorine (chloro), bromine (bromo) or iodine (iodo).

As used herein, the term "$C_1$-$C_8$ alkyl" refers to a straight or branched hydrocarbon chain radical consisting solely of carbon and hydrogen atoms, containing no unsaturation, having from one to eight carbon atoms, and which is attached to the rest of the molecule by a single bond. "$C_1$-$C_6$alkyl", "$C_1$-$C_4$alkyl" and "$C_1$-$C_3$alkyl" are to be construed accordingly. Examples of $C_1$-$C_8$alkyl include, but are not limited to, methyl, ethyl, n-propyl, and the isomers thereof, for example, iso-propyl. A "$C_1$-$C_6$alkylene" group refers to the corresponding definition of $C_1$-$C_6$alkyl, except that such radical is attached to the rest of the molecule by two single bonds.

As used herein, the term "$C_1$-$C_6$alkoxy" refers to a radical of the formula —$OR_a$ where $R_a$ is a $C_1$-$C_6$alkyl radical as generally defined above. The terms "$C_1$-$C_4$alkoxy" and "$C_1$-$C_3$alkoxy" are to be construed accordingly. Examples of $C_1$-$C_6$alkoxy include, but are not limited to, methoxy, ethoxy, 1-methylethoxy (iso-propoxy), and propoxy.

As used herein, the term "$C_1$-$C_6$alkoxy$C_1$-$C_6$alkyl" refers to a radical of the formula $R_bOR_a$— wherein $R_b$ is a $C_1$-$C_6$alkyl radical as generally defined above, and $R_a$ is a $C_1$-$C_6$alkylene radical as generally defined above. "$C_1$-$C_6$alkoxy$C_1$-$C_6$alkyl", "$C_1$-$C_4$alkoxy$C_1$-$C_4$alkyl", "$C_1$-$C_4$alkoxy$C_1$-$C_3$alkyl", "$C_1$-$C_4$alkoxy$C_1$-$C_2$alkyl", and "$C_3$-$C_4$alkoxy$C_1$-$C_2$alkyl" are to be construed accordingly. Examples of $C_1$-$C_6$alkoxy$C_1$-$C_6$alkyl include, but are not limited to isopropoxymethyl, tert-butoxymethyl, 1-methoxyethyl, 1-isopropoxyethyl, 1-tert-butoxyethyl.

As used herein, the term "$C_1$-$C_6$alkoxycarbonyl" refers to a radical of the formula $R_aOC(O)$—, wherein $R_a$ is a $C_1$-$C_6$ radical as generally defined above. "$C_1$-$C_4$alkoxycarbonyl" and "$C_1$-$C_3$alkoxycarbonyl" are to be construed accordingly.

As used herein, the term "$C_1$-$C_6$alkoxycarbonyl$C_1$-$C_4$alkyl" refers to a radical of the formula $R_aOC(O)R_b$—, wherein $R_a$ is a $C_1$-$C_6$alkyl radical as generally defined above, and $R_b$ is a $C_1$-$C_4$alkylene radical as generally defined above.

As used herein, the term "$C_1$-$C_6$alkoxy$C_1$-$C_6$alkycarbonyl" refers to a radical of the formula $R_aOR_bC(O)$—, wherein $R_a$ is a $C_1$-$C_6$alkyl radical as generally defined above, and $R_b$ is a $C_1$-$C_6$alkylene radical as generally defined above.

As used herein, the term "$C_1$-$C_6$alkylsulfanyl$C_1$-$C_6$alkyl" refers to a radical of the formula $R_aSR_b$—, wherein $R_a$ is a $C_1$-$C_6$alkyl radical as generally defined above, and $R_b$ is a $C_1$-$C_6$alkylene radical as generally defined above.

As used herein, the term "$C_1$-$C_6$alkylsulfinyl$C_1$-$C_6$alkyl" refers to a radical of the formula $R_aS(O)R_b$— wherein $R_a$ is a $C_1$-$C_6$alkyl radical as generally defined above, and $R_b$ is a $C_1$-$C_6$alkylene radical as generally defined above.

As used herein, the term "$C_1$-$C_6$alkylsulfanyl$C_1$-$C_6$alkylcarbonyl" refers to a radical of the formula $R_aSR_bC(O)$—, wherein $R_a$ is a $C_1$-$C_6$alkyl radical as generally defined above, and $R_b$ is a $C_1$-$C_6$alkylene radical as generally defined above.

As used herein, the term "$C_1$-$C_6$alkylsulfinyl$C_1$-$C_6$alkylcarbonyl" refers to a radical of the formula $R_aS(O)R_bC(O)$—, wherein $R_a$ is a $C_1$-$C_6$alkyl radical as generally defined above, and $R_b$ is a $C_1$-$C_6$alkylene radical as generally defined above.

As used herein, the term "$C_1$-$C_6$alkylsulfonyl$C_1$-$C_6$alkylcarbonyl" refers to a radical of the formula $R_aS(O)_2R_bC(O)$—, wherein $R_a$ is a $C_1$-$C_6$alkyl radical as generally defined above, and $R_b$ is a $C_1$-$C_6$alkylene radical as generally defined above.

As used herein, the term "heterocyclyl" refers to a stable 4-, 5- or 6-membered non-aromatic monocyclic ring which comprises 1, 2 or 3 heteroatoms, wherein the heteroatoms are individually selected from nitrogen, oxygen and sulfur. The heterocyclyl radical may be bonded to the rest of the molecule via a carbon atom or heteroatom. Examples of heterocyclyl include, but are not limited to, aziridinyl, azetidinyl, oxetanyl, thietanyl, tetrahydrofuryl, pyrrolidinyl, pyrazolidinyl, imidazolidnyl, piperidinyl, piperazinyl, morpholinyl, dioxolanyl, dithiolanyl and thiazolidinyl.

As used herein, the term "heterocyclylcarbonyl" refers to a radical of the formula $R_aC(O)$—, wherein $R_a$ is a heterocyclyl moiety as defined above.

The presence of one or more possible asymmetric carbon atoms in a compound of formula (I) means that the compounds may occur in optically isomeric forms, i.e., enantiomeric or diastereomeric forms. Also, atropisomers may occur as a result of restricted rotation about a single bond. Formula (I) is intended to include all those possible isomeric forms and mixtures thereof. The present invention includes all those possible isomeric forms and mixtures thereof for a compound of formula (I). Likewise, formula (I) is intended to include all possible tautomers. The present invention includes all possible tautomeric forms for a compound of formula (I).

In each case, the compounds of formula (I) according to the invention are in free form, in oxidized form as an N-oxide, or in salt form, e.g., an agronomically usable salt form.

N-oxides are oxidized forms of tertiary amines or oxidized forms of nitrogen-containing heteroaromatic compounds. They are described for instance in the book "Heterocyclic N-oxides" by A. Albini and S. Pietra, CRC Press, Boca Raton (1991).

The following list provides definitions, including preferred definitions, for substituents A, $R^1$, $R^2$, $R^3$, $R^4$, $R^5$, $R^6$, $R^7$ and $R^8$ with reference to compounds of Formula (I). For any one of these substituents, any of the definitions given below may be combined with any definition of any other substituent given below or elsewhere in this document.

A is C—H or N. In one set of embodiments, A is C—H. In another set of embodiments, A is N.

$R^1$ is $C_1$-$C_4$alkoxy$C_1$-$C_2$alkyl, $C_1$-$C_6$alkylsulfanyl$C_1$-$C_6$alkyl, $C_1$-$C_6$alkylsulfinyl$C_1$-$C_6$alkyl, $C_1$-$C_6$alkylsulfonyl$C_1$-$C_6$alkyl, or heterocyclyl, wherein the heterocyclyl moiety is a 4-, 5- or 6-membered non-aromatic monocyclic ring comprising 1, 2 or 3 heteroatoms individually selected from nitrogen, oxygen and sulfur.

Preferably, $R^1$ is $C_1$-$C_4$alkoxy$C_1$-$C_2$alkyl, $C_1$-$C_3$alkylsulfanyl$C_1$-$C_3$alkyl, $C_1$-$C_3$alkylsulfinyl$C_1$-$C_3$alkyl, $C_1$-$C_3$alkylsulfonyl$C_1$-$C_3$alkyl, or heterocyclyl, wherein the heterocyclyl moiety is a 4-, 5-, or 6-membered non-aromatic monocyclic ring comprising 1 or 2 heteroatoms individually selected from nitrogen and oxygen.

More preferably, $R^1$ is $C_1$-$C_3$alkoxy$C_1$-$C_2$alkyl, $C_1$-$C_3$alkylsulfanyl$C_1$-$C_3$alkyl, $C_1$-$C_3$alkylsulfinyl$C_1$-$C_3$alkyl, $C_1$-$C_3$alkylsulfonyl$C_1$-$C_3$alkyl, or heterocyclyl, wherein the heterocyclyl moiety is a 4-, 5- or 6-membered non-aromatic monocyclic ring comprising a single oxygen atom.

More preferably still, $R^1$ is $C_3$-$C_4$alkoxy$C_1$-$C_2$alkyl, $C_1$-$C_3$alkylsulfanyl$C_1$-$C_3$alkyl, $C_1$-$C_3$alkylsulfinyl$C_1$-$C_3$alkyl, $C_1$-$C_3$alkylsulfonyl$C_1$-$C_3$alkyl, or heterocyclyl, wherein the heterocyclyl moiety is a 4-, 5-, or 6-membered non-aromatic monocyclic ring comprising 1 or 2 heteroatoms individually selected from nitrogen and oxygen.

Even more preferably still, $R^1$ is isopropoxymethyl, tert-butoxymethyl, 1-methoxyethyl, 1-isopropoxyethyl, 1-tert-butoxyethyl, $C_1$-$C_3$alkylsulfanyl$C_1$-$C_3$alkyl, $C_1$-$C_3$alkylsulfinyl$C_1$-$C_3$alkyl, $C_1$-$C_3$alkylsulfonyl$C_1$-$C_3$alkyl, or heterocyclyl, wherein the heterocyclyl moiety is a 4-, 5-, or 6-membered non-aromatic monocyclic ring comprising 1 or 2 heteroatoms individually selected from nitrogen and oxygen.

In a further preferable embodiment, $R^1$ is isopropoxymethyl, tert-butoxymethyl, 1-methoxyethyl, 1-isopropoxyethyl, 1-tert-butoxyethyl, 1-methylsulfonylethyl, oxetane-3-yl, tetrahydrofuran-2-yl, tetrahydrofuran-3-yl, or tetrahydropyran-4-yl.

In one embodiment, $R^1$ is $C_1$-$C_6$alkoxy$C_1$-$C_6$alkyl, $C_1$-$C_6$alkylsulfanyl$C_1$-$C_6$alkyl, $C_1$-$C_6$alkylsulfinyl$C_1$-$C_6$alkyl, $C_1$-$C_6$alkylsulfonyl$C_1$-$C_6$alkyl, or heterocyclyl, wherein the heterocyclyl moiety is a 4-, 5- or 6-membered non-aromatic monocyclic ring comprising 1, 2 or 3 heteroatoms individually selected from nitrogen, oxygen and sulfur.

Preferably, $R^1$ is $C_1$-$C_4$alkoxy$C_1$-$C_4$alkyl, $C_1$-$C_4$alkylsulfanyl$C_1$-$C_4$alkyl, $C_1$-$C_4$alkylsulfinyl$C_1$-$C_4$alkyl, $C_1$-$C_4$alkylsulfonyl$C_1$-$C_4$alkyl, or heterocyclyl, wherein the heterocyclyl moiety is a 4-, 5- or 6-membered non-aromatic monocyclic ring comprising 1 or 2 heteroatoms individually selected from nitrogen, oxygen and sulfur.

More preferably, $R^1$ is $C_1$-$C_4$alkoxy$C_1$-$C_3$alkyl, $C_1$-$C_3$alkylsulfanyl$C_1$-$C_3$alkyl, $C_1$-$C_3$alkylsulfinyl$C_1$-$C_3$alkyl, $C_1$-$C_3$alkylsulfonyl$C_1$-$C_3$alkyl, or heterocyclyl, wherein the heterocyclyl moiety is a 4- or 5-membered non-aromatic monocyclic ring comprising 1 or 2 heteroatoms individually selected from nitrogen and oxygen.

Even more preferably, $R^1$ is $C_1$-$C_3$alkoxy$C_1$-$C_3$alkyl, $C_1$-$C_3$alkylsulfanyl$C_1$-$C_3$alkyl, $C_1$-$C_3$alkylsulfinyl$C_1$-$C_3$alkyl, $C_1$-$C_3$alkylsulfonyl$C_1$-$C_3$alkyl, or heterocyclyl, wherein the heterocyclyl moiety is a 4- or 5-membered non-aromatic monocyclic ring comprising a single oxygen atom.

Even more preferably still, $R^1$ is isopropoxymethyl, tert-butoxymethyl, 1-methoxyethyl, 1-isopropoxyethyl, 1-tert-butoxyethyl, 1-methylsulfanylethyl, 1-methylsulfinylethyl, 1-methylsulfonylethyl, oxetane-3-yl, tetrahydrofuran-2-yl, or tetrahydrofuran-3-yl.

Most preferably, $R^1$ is isopropoxymethyl, tert-butoxymethyl, 1-methoxyethyl, 1-isopropoxyethyl, 1-methylsulfonylethyl, oxetane-3-yl, tetrahydrofuran-2-yl, or tetrahydrofuran-3-yl.

In one set of embodiments, $R^1$ is $C_1$-$C_6$alkylsulfanyl$C_1$-$C_6$alkyl, $C_1$-$C_6$alkylsulfinyl$C_1$-$C_6$alkyl, $C_1$-$C_6$alkylsulfonyl$C_1$-$C_6$alkyl, or heterocyclyl, wherein the heterocyclyl moiety is a 4-, 5- or 6-membered non-aromatic monocyclic ring comprising 1, 2 or 3 heteroatoms individually selected from nitrogen, oxygen and sulfur.

In another set of embodiments, $R^1$ is $C_1$-$C_4$alkylsulfanyl$C_1$-$C_4$alkyl, $C_1$-$C_4$alkylsulfinyl$C_1$-$C_4$alkyl, $C_1$-$C_4$alkylsulfonyl$C_1$-$C_4$alkyl, or heterocyclyl, wherein the heterocyclyl moiety is a 4-, 5- or 6-membered non-aromatic monocyclic ring comprising 1 or 2 heteroatoms individually selected from nitrogen, oxygen and sulfur.

In a further set of embodiments, $R^1$ is $C_1$-$C_3$alkylsulfanyl$C_1$-$C_3$alkyl, $C_1$-$C_3$alkylsulfinyl$C_1$-$C_3$alkyl, $C_1$-$C_3$alkylsulfonyl$C_1$-$C_3$alkyl, or heterocyclyl, wherein the heterocyclyl moiety is a 4-, 5-, or 6-membered non-aromatic monocyclic ring comprising 1 or 2 heteroatoms individually selected from nitrogen and oxygen.

In a further set of embodiments, $R^1$ is $C_1$-$C_3$alkylsulfanyl$C_1$-$C_3$alkyl, $C_1$-$C_3$alkylsulfinyl$C_1$-$C_3$alkyl, $C_1$-$C_3$alkylsulfonyl$C_1$-$C_3$alkyl, or heterocyclyl, wherein the heterocyclyl moiety is a 4- or 5-membered non-aromatic monocyclic ring comprising 1 or 2 heteroatoms individually selected from nitrogen and oxygen.

In a further still set of embodiments, $R^1$ is $C_1$-$C_3$alkylsulfanyl$C_1$-$C_3$alkyl, $C_1$-$C_3$alkylsulfinyl$C_1$-$C_3$alkyl, $C_1$-$C_3$alkylsulfonyl$C_1$-$C_3$alkyl, or heterocyclyl, wherein the heterocyclyl moiety is a 4- or 5-membered non-aromatic monocyclic ring comprising a single oxygen atom.

In a preferable set of embodiments, $R^1$ is 1-methylsulfonylethyl, oxetane-3-yl, tetrahydrofuran-2-yl, tetrahydrofuran-3-yl, or tetrahydropyran-4-yl.

In a more preferable set of embodiments, $R^1$ is 1-methylsulfanylethyl, 1-methylsulfinylethyl, 1-methylsulfonylethyl, oxetane-3-yl, tetrahydrofuran-2-yl, or tetrahydrofuran-3-yl.

In a most preferable set of embodiments, $R^1$ is 1-methylsulfonylethyl, oxetane-3-yl, tetrahydrofuran-2-yl, or tetrahydrofuran-3-yl.

In a further set of preferable embodiments, $R^1$ is $C_3$-$C_4$alkoxy$C_1$-$C_3$alkyl, $C_1$-$C_3$alkylsulfanyl$C_1$-$C_3$alkyl, $C_1$-$C_3$alkylsulfinyl$C_1$-$C_3$alkyl, $C_1$-$C_3$alkylsulfonyl$C_1$-$C_3$alkyl, or heterocyclyl, wherein the heterocyclyl moiety is a 4- or 5-membered non-aromatic monocyclic ring comprising 1 or 2 heteroatoms individually selected from nitrogen and oxygen.

Preferably, $R^1$ is isopropoxymethyl, tert-butoxymethyl, 1-isopropoxyethyl, 1-tert-butoxyethyl, 1-methylsulfanylethyl, 1-methylsulfinylethyl, 1-methylsulfonylethyl, oxetane-3-yl, tetrahydrofuran-2-yl, or tetrahydrofuran-3-yl. More preferably, $R^1$ is isopropoxymethyl, tert-butoxymethyl, 1-isopropoxyethyl, 1-methylsulfonylethyl, oxetane-3-yl, tetrahydrofuran-2-yl, or tetrahydrofuran-3-yl.

$R^2$ is hydrogen or halogen. Preferably, $R^2$ is hydrogen, chloro, bromo or fluoro. More preferably, $R^2$ is hydrogen or fluoro. In one set of embodiments, $R^2$ is hydrogen. In a further set of embodiments, $R^2$ is fluoro.

$R^3$ is $C_1$-$C_6$alkyl. Preferably, $R^3$ is $C_1$-$C_6$alkyl. More preferably, $R^3$ is $C_1$-$C_3$alkyl. Even more preferably, $R^3$ is methyl, ethyl or isopropyl. Most preferably, $R^3$ is methyl.

$R^4$, $R^5$, $R^6$ are each independently hydrogen or $C_1$-$C_4$alkyl. Preferably, $R^4$, $R^5$, $R^6$ are each independently hydrogen or $C_1$-$C_3$alkyl. More preferably, $R^4$, $R^5$, $R^6$ are each independently hydrogen or methyl.

In one set of embodiments, $R^4$ is hydrogen, and $R^5$ and $R^6$ are both methyl.

$R^7$ is hydrogen, $C_1$-$C_4$alkyl, $C_1$-$C_6$alkoxycarbonyl$C_1$-$C_4$alkyl, $C_1$-$C_6$alkoxycarbonyl, or $C_1$-$C_6$alkoxy. Preferably, $R^7$ is hydrogen, $C_1$-$C_3$alkyl, $C_1$-$C_4$alkoxycarbonyl$C_1$-$C_3$alkyl, $C_1$-$C_4$alkoxycarbonyl, or $C_1$-$C_4$alkoxy. More preferably, $R^7$ is hydrogen, $C_1$-$C_3$alkyl, $C_1$-$C_3$alkoxycarbonyl$C_1$-$C_2$alkyl, $C_1$-$C_3$alkoxycarbonyl, or $C_1$-$C_3$alkoxy. Even more preferably, $R^7$ is hydrogen, methyl, methoxycarbonylmethyl, methoxycarbonyl, or methoxy. More preferably still, $R^7$ is hydrogen or methyl, most preferably, $R^7$ is hydrogen.

$R^8$ is hydrogen, $C_1$-$C_6$alkoxy$C_1$-$C_6$alkycarbonyl, $C_1$-$C_6$alkylsulfanyl$C_1$-$C_6$alkylcarbonyl, $C_1$-$C_6$alkylsulfinyl$C_1$-$C_6$alkycarbonyl, $C_1$-$C_6$alkylsulfonyl$C_1$-$C_6$alkycarbonyl, or heterocyclylcarbonyl, wherein the heterocyclyl moiety is a 4-, 5- or 6-membered non-aromatic monocyclic ring comprising 1, 2 or 3 heteroatoms individually selected from nitrogen, oxygen and sulfur.

Preferably, $R^8$ is hydrogen, $C_1$-$C_4$alkoxy$C_1$-$C_4$alkycarbonyl, $C_1$-$C_4$alkylsulfanyl$C_1$-$C_4$alkylcarbonyl, $C_1$-$C_4$alkylsulfinyl$C_1$-$C_4$alkycarbonyl, $C_1$-$C_4$alkylsulfonyl$C_1$-$C_4$alkycarbonyl, or heterocyclylcarbonyl, wherein the heterocyclyl moiety is a 4-, 5- or 6-membered non-aromatic monocyclic ring comprising 1 or 2 heteroatoms individually selected from nitrogen, oxygen and sulfur.

More preferably, $R^8$ is hydrogen, $C_1$-$C_3$alkoxy$C_1$-$C_3$alkycarbonyl, $C_1$-$C_3$alkylsulfanyl$C_1$-$C_3$alkylcarbonyl, $C_1$-$C_3$alkylsulfinyl$C_1$-$C_3$alkycarbonyl, $C_1$-$C_3$alkylsulfonyl$C_1$-$C_3$alkycarbonyl, or heterocyclylcarbonyl, wherein the heterocyclyl moiety is a 4- or 5-membered non-aromatic monocyclic ring comprising 1 or 2 heteroatoms individually selected from nitrogen and oxygen.

Even more preferably, $R^8$ is hydrogen, or heterocyclylcarbonyl, wherein the heterocyclyl moiety is a 4- or 5-membered non-aromatic monocyclic ring comprising a single oxygen atom.

Even more preferably still, $R^8$ is hydrogen or tetrahydrofuran-3-carbonyl. Most preferably, $R^8$ is hydrogen.

In a compound of formula (I) according to the present invention, preferably:

A is C—H or N;

$R^1$ is $C_3$-$C_4$alkoxy$C_1$-$C_3$alkyl, $C_1$-$C_3$alkylsulfanyl$C_1$-$C_3$alkyl, $C_1$-$C_3$alkylsulfinyl$C_1$-$C_3$alkyl, $C_1$-$C_3$alkylsulfonyl$C_1$-$C_3$alkyl, or heterocyclyl, wherein the heterocyclyl moiety is a 4- or 5-membered non-aromatic monocyclic ring comprising a single oxygen atom;

$R^2$ is hydrogen or fluoro;

$R^3$ is methyl;

$R^4$, $R^5$, and $R^6$ are each independently hydrogen or methyl;

$R^7$ is hydrogen; and $R^8$ is hydrogen or heterocyclylcarbonyl, wherein the heterocyclyl moiety is a 4- or 5-membered non-aromatic monocyclic ring comprising a single oxygen atom.

More preferably, A is N;

$R^1$ is $C_3$-$C_4$alkoxy$C_1$-$C_3$alkyl, $C_1$-$C_3$alkylsulfanyl$C_1$-$C_3$alkyl, $C_1$-$C_3$alkylsulfinyl$C_1$-$C_3$alkyl, $C_1$-$C_3$alkylsulfonyl$C_1$-$C_3$alkyl, or heterocyclyl, wherein the heterocyclyl moiety is a 4- or 5-membered non-aromatic monocyclic ring comprising a single oxygen atom;

$R^2$ is hydrogen or fluoro;

$R^3$ is methyl;

$R^4$, $R^5$, and $R^6$ are each independently hydrogen or methyl;

$R^7$ is hydrogen; and $R^8$ is hydrogen or tetrahydrofuranyl.

Even more preferably, A is N;

$R^1$ is $C_1$-$C_3$alkylsulfanyl$C_1$-$C_3$alkyl, $C_1$-$C_3$alkylsulfinyl$C_1$-$C_3$alkyl, $C_1$-$C_3$alkylsulfonyl$C_1$-$C_3$alkyl, or heterocyclyl, wherein the heterocyclyl moiety is a 4- or 5-membered non-aromatic monocyclic ring comprising a single oxygen atom;

$R^2$ is hydrogen or fluoro;

$R^3$ is methyl;

$R^4$ is hydrogen;

$R^5$ and $R^6$ are both methyl;

$R^7$ is hydrogen; and $R^8$ is hydrogen.

In a further set of preferable embodiments, in a compound of formula (I) according to the present invention, preferably, A is N;

$R^1$ is $C_1$-$C_4$alkoxy$C_1$-$C_2$alkyl, $C_1$-$C_6$alkylsulfanyl$C_1$-$C_6$alkyl, $C_1$-$C_6$alkylsulfinyl$C_1$-$C_6$alkyl, $C_1$-$C_6$alkylsulfonyl$C_1$-$C_6$alkyl, or heterocyclyl, wherein the heterocyclyl moiety is a 4-, 5- or 6-membered non-aromatic monocyclic ring comprising 1, 2 or 3 heteroatoms individually selected from nitrogen, oxygen and sulfur;

$R^2$ is hydrogen or fluoro;

$R^3$ is methyl;

$R^4$ is hydrogen;

$R^5$ and $R^6$ are both methyl;

$R^7$ is hydrogen; and $R^8$ is hydrogen.

More preferably, A is N;

$R^1$ is isopropoxymethyl, tert-butoxymethyl, 1-methoxyethyl, 1-isopropoxyethyl, 1-tert-butoxyethyl, $C_1$-$C_3$alkylsulfanyl$C_1$-$C_3$alkyl, $C_1$-$C_3$alkylsulfinyl$C_1$-$C_3$alkyl, $C_1$-$C_3$alkylsulfonyl$C_1$-$C_3$alkyl, or heterocyclyl, wherein the heterocyclyl moiety is a 4-, 5-, or 6-membered non-aromatic monocyclic ring comprising 1 or 2 heteroatoms individually selected from nitrogen and oxygen;

$R^2$ is hydrogen or fluoro;

$R^3$ is methyl;

$R^4$ is hydrogen;

$R^5$ and $R^6$ are both methyl;

$R^7$ is hydrogen; and $R^8$ is hydrogen.

Preferably, the compound of formula (I) is selected from:

2-[(2,6-difluoro-4-pyridyl)-(tetrahydrofuran-3-carbonyl)amino]-N-(2,2-dimethylcyclobutyl)-5-methyl-N-(tetrahydrofuran-3-carbonyl)thiazole-4-carboxamide (P-1);

2-[(2,6-difluoro-4-pyridyl)-(tetrahydrofuran-2-carbonyl)amino]-N-(2,2-dimethylcyclobutyl)-5-methyl-thiazole-4-carboxamide (P-2);

2-[(2,6-difluoro-4-pyridyl)-(tetrahydrofuran-3-carbonyl)amino]-N-(2,2-dimethylcyclobutyl)-5-methyl-thiazole-4-carboxamide (P-3);

2-[(2,6-difluoro-4-pyridyl)-(oxetane-3-carbonyl)amino]-N-(2,2-dimethylcyclobutyl)-5-methyl-thiazole-4-carboxamide (P-4);

2-[2-tert-butoxypropanoyl-(2,6-difluoro-4-pyridyl)amino]-N-(2,2-dimethylcyclobutyl)-5-methyl-thiazole-4-carboxamide (P-5);

2-[(2,6-difluoro-4-pyridyl)-(2-isopropoxypropanoyl)amino]-N-(2,2-dimethylcyclobutyl)-5-methyl-thiazole-4-carboxamide (P-6);

2-[(2-tert-butoxyacetyl)-(2,6-difluoro-4-pyridyl)amino]-N-(2,2-dimethylcyclobutyl)-5-methyl-thiazole-4-carboxamide (P-7);

2-[(2,6-difluoro-4-pyridyl)-(2-isopropoxyacetyl)amino]-N-(2,2-dimethylcyclobutyl)-5-methyl-thiazole-4-carboxamide (P-8);

2-[(2,6-difluoro-4-pyridyl)-(2-methoxypropanoyl)amino]-N-(2,2-dimethylcyclobutyl)-5-methyl-thiazole-4-carboxamide (P-9);

2-[(2,6-difluoro-4-pyridyl)-(2-methylsulfonylpropanoyl)amino]-N-(2,2-dimethylcyclobutyl)-5-methyl-thiazole-4-carboxamide (P-10); and 2-[(2,6-difluoro-4-pyridyl)-(tetrahydropyran-4-carbonyl)amino]-N-(2,2-dimethylcyclobutyl)-5-methyl-thiazole-4-carboxamide (P-11).

Compounds of the present invention can be made as shown in the following schemes, in which, unless otherwise stated, the definition of each variable is as defined above for a compound of Formula (I).

The compounds of formula (Ia) according to the invention, wherein $R^1$, $R^2$, $R^3$, $R^4$, $R^5$, $R^6$, and $R^7$ are as defined for formula (I), and $R^8$ is hydrogen, can be obtained by transformation of a compound of formula (II), wherein A, $R^2$, $R^3$, $R^4$, $R^5$, $R^5$, and $R^7$ are as defined for formula (I), with a compound of formula (III), wherein $R^1$ is as defined for formula (I) and Xa is halogen, preferably bromo or chloro, either by thermal heating, or with the aid of a base. This is shown in Scheme 1 (below).

Scheme 1

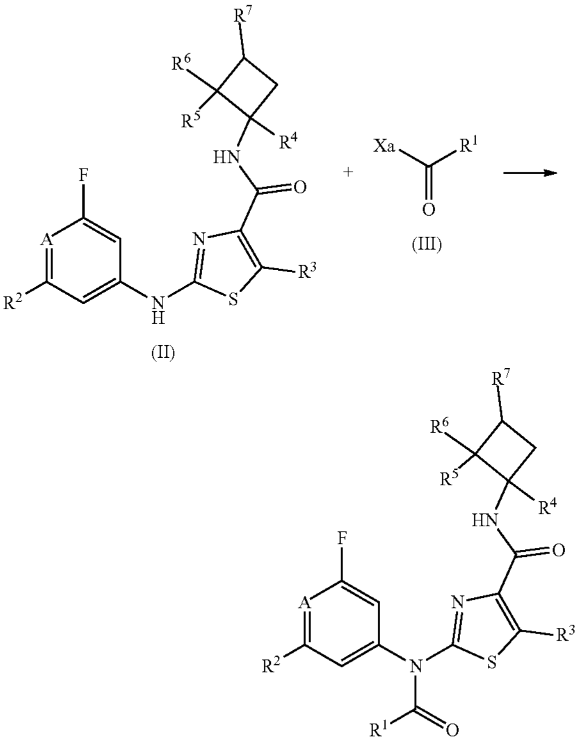

(II) (III) (Ia)

Those skilled in the art will recognise that the conditions used to prepare compounds of formula (Ia) will depend on the stoichiometry of the reaction. For example, reacting 1-1.5 equivalents of compounds of formula (III) with 1 equivalent of compounds of formula (II) will generate predominantly compounds of formula (Ia), whereas reacting 2-2.1 equivalents of compounds of formula (III) with 1 equivalent of compounds of formula (II) will generate compounds of formula (Ib), wherein $R^{8a}$ is $C_1$-$C_6$alkoxy$C_1$-$C_6$alkycarbonyl, $C_1$-$C_6$alkylsulfanyl$C_1$-$C_6$alkylcarbonyl, $C_1$-$C_6$alkylsulfinyl$C_1$-$C_6$alkycarbonyl, $C_1$-$C_6$alkylsulfonyl$C_1$-$C_6$alkycarbonyl, or heterocyclylcarbonyl, wherein the heterocyclyl is a 4-, 5- or 6-membered non-aromatic monocyclic ring comprising 1, 2 or 3 heteroatoms individually selected from nitrogen, oxygen and sulfur. This is illustrated in Scheme 2 (below).

Scheme 2

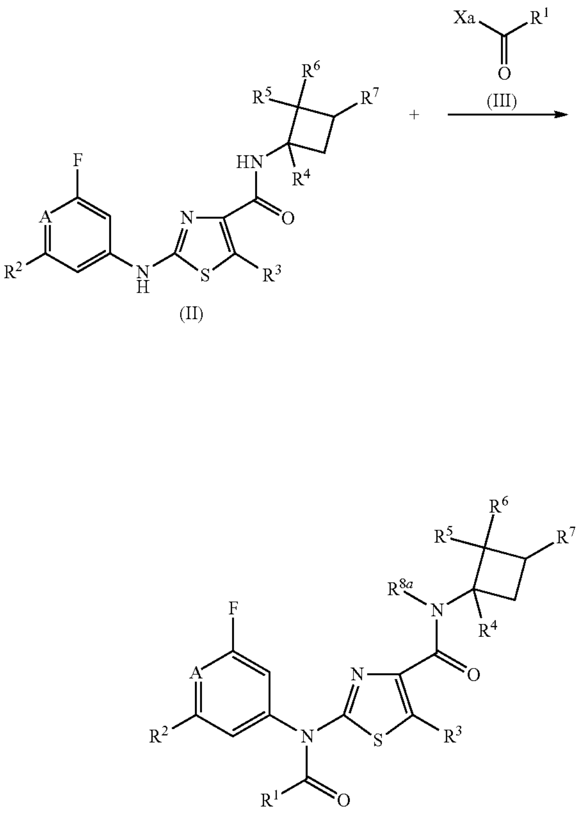

(III) (II) (Ib)

$R^{8a}$ is 

The compounds of formula (II), wherein A, $R^2$, $R^3$, $R^4$, $R^5$, $R^6$, and $R^7$ are as defined for formula (I), can be obtained by transformation of a compound of formula (IV), wherein A and $R^2$ are as defined for formula (I), with a compound of formula (V), wherein $R^3$, $R^4$, $R^5$, $R^6$, and $R^7$ are as defined for Formula (I) and Xb is halogen, preferably bromo or chloro, either by thermal heating, or with the aid of a base or under the conditions of the transition metal catalysed Buchwald-Hartwig amination. This is shown in Scheme 3 (below). Such compounds of formula (II) have been described in WO 2019/105933.

Scheme 3

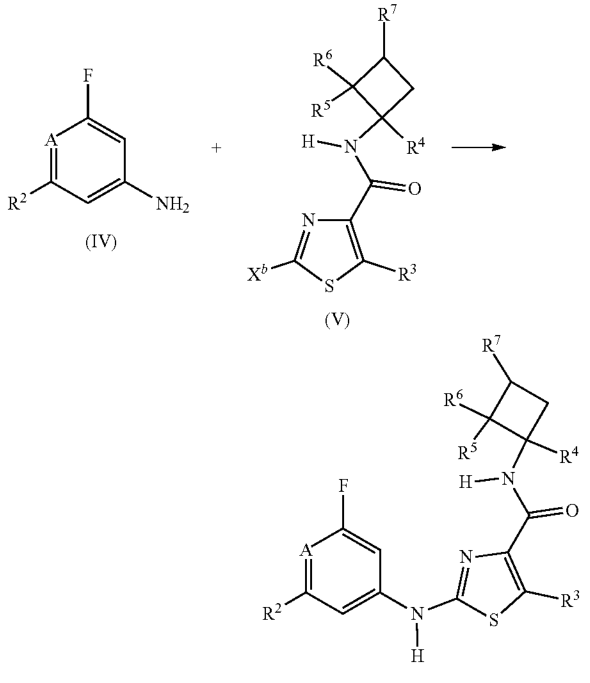

(IV) (V) (II)

The compounds of formula (V), wherein $R^3$, $R^4$, $R^5$, $R^6$, and $R^7$ are as defined for formula (I) and Xb is halogen, preferably bromo or chloro, can be obtained by transformation of a compound of formula (VI), wherein $R^2$ is as defined for formula (I) and Xb is halogen, preferably bromo, and a compound of formula (VII), wherein $R^4$, $R^5$, $R^6$, and $R^7$ is as defined for formula (I), either via an intermediate acid chloride or directly with a peptide coupling agent. This is shown in Scheme 4 (below).

Scheme 4

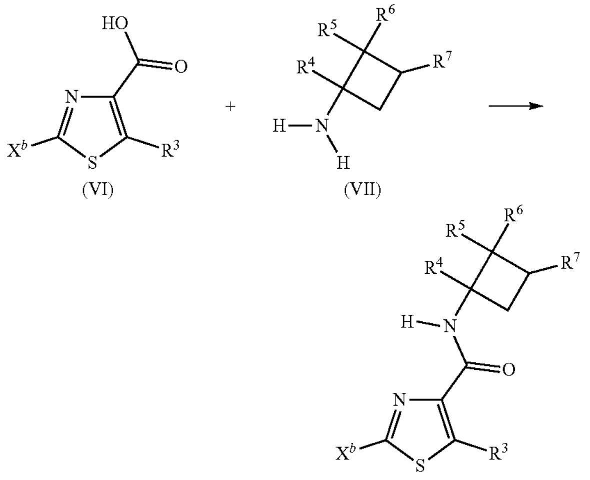

(VI) (VII) (V)

The compounds of formula (VI), wherein $R^3$ is as defined for formula (I) and Xb is halogen, preferably bromo or chloro, can be obtained by transformation of a compound of Formula (VIII), wherein $R^3$ is as defined for formula (I), Xb is halogen, preferably bromo or chloro, and $R^9$ is $C_1$-$C_6$alkyl, and a base. This is shown in Scheme 5 (below).

Scheme 5

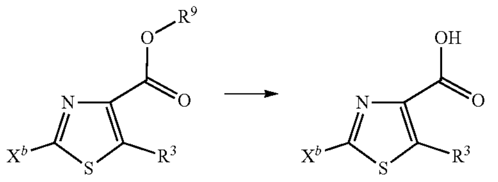

(VIII) (VI)

Alternatively, the compounds of formula (II), wherein $R^2$ and A are as defined for formula (I), can be obtained by transformation of a compound of formula (IX), wherein $R^2$, $R^3$, and A are as defined for formula (I), with a compound of formula (VII), wherein $R^4$, $R^5$, $R^6$, and $R^7$ are as defined for formula (I), either via an intermediate acid chloride or directly with an peptide coupling agent. This is shown in Scheme 6 (below).

Scheme 6

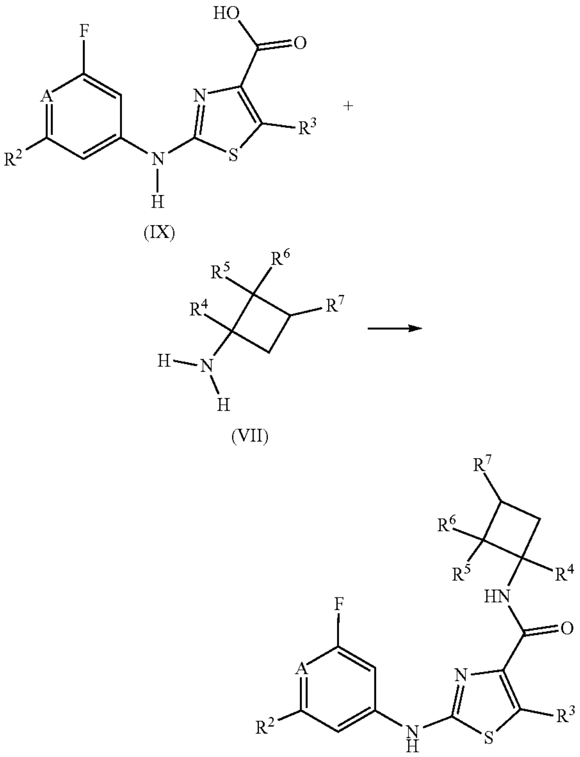

(IX) (VII) (II)

The compounds of formula (IX), wherein $R^2$, A and $R^3$ are as defined for formula (I), can be obtained by transformation of a compound of formula (X), wherein $R^2$, $R^3$ and A are as defined for formula (I) and $R^{10}$ is $C_1$-$C_6$alkyl, with a base. This is shown in Scheme 7 (below).

Scheme 7

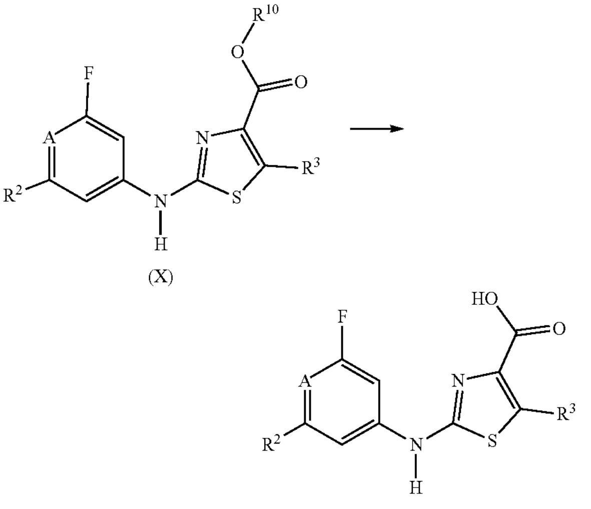

(X) (IX)

The compounds of formula (X), wherein $R^2$, A, and $R^3$ are as defined for formula (I) and $R^{10}$ is $C_1$-$C_6$alkyl, can be obtained by transformation of a compound of formula (IV), wherein A and $R^2$ are as defined for formula (I), with a compound of formula (VII), wherein $R^3$ is as defined for formula (I), Xb is halogen, preferably bromo or chloro, and $R^{10}$ is $C_1$-$C_6$alkyl, either by thermal heating, or with the aid of a base or under the conditions of the transition metal catalysed Buchwald-Hartwig amination. This is shown in Scheme 8 (below).

Scheme 8

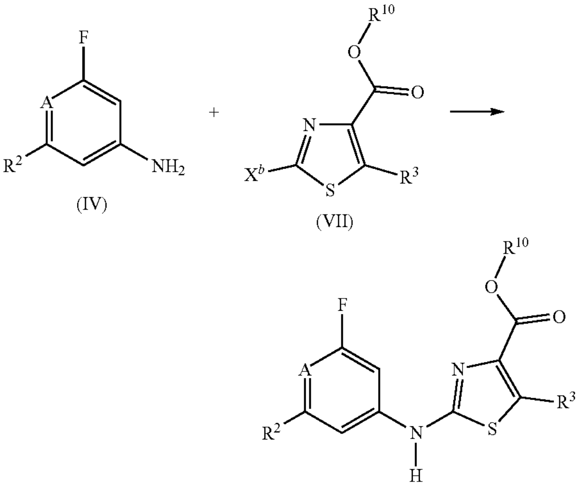

(IV) (VII) (X)

Alternatively, the compounds of formula (X), wherein $R^2$, A, and $R^3$ are as defined for formula (I) and $R^{10}$ is $C_1$-$C_6$alkyl, can be obtained by transformation of a compound of formula (XI), wherein $R^2$ and A are as defined for formula (I) and Xc is halogen, preferably bromo or iodo, with a compound of formula (XII), wherein $R^3$ is as defined for formula (I) and $R^{10}$ is $C_1$-$C_6$alkyl, under the conditions of the transition metal catalysed Buchwald-Hartwig amination. This is shown in Scheme 9 (below).

Scheme 9

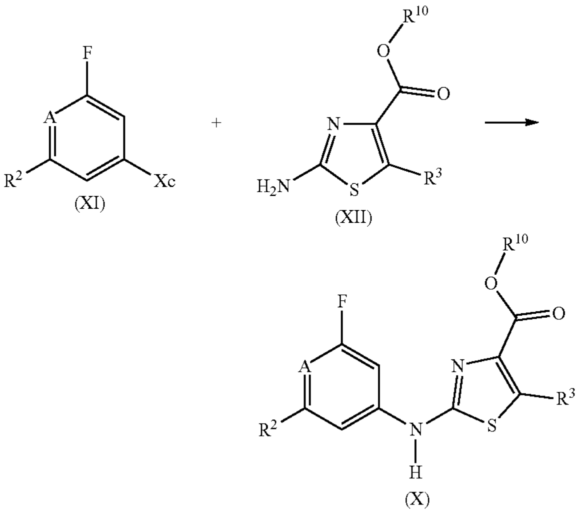

(XI) (XII) (X)

Alternatively, the compounds of formula (II), wherein A, $R^2$, $R^3$, $R^4$, $R^1$, $R^6$, and $R^7$ are as defined for formula (I), can be obtained by transformation of a compound of formula (XI), wherein A and $R^2$ are as defined for formula (I) and Xc is halogen, preferably bromo or iodo, with a compound of formula (XIII), wherein $R^3$, $R^4$, $R^1$, $R^6$, and $R^7$ are as defined for formula (I), either by thermal heating, or with the aid of a base or under the conditions of the transition metal catalysed Buchwald-Hartwig amination. This is shown in Scheme 10 (below).

Scheme 10

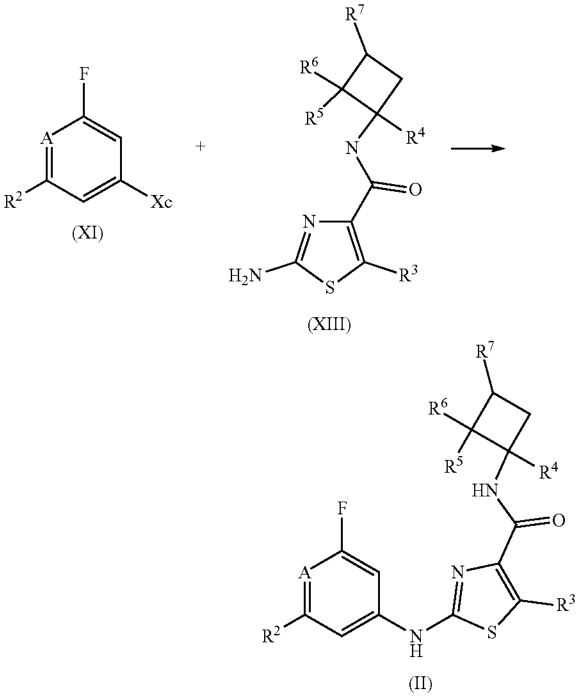

(XI) (XIII) (II)

Surprisingly, it has now been found that the novel compounds of formula (I) have, for practical purposes, a very advantageous level of biological activity for protecting plants against diseases that are caused by fungi.

The compounds of formula (I) can be used in the agricultural sector and related fields of use, e.g., as active ingredients for controlling plant pests or on non-living materials for control of spoilage microorganisms or organisms potentially harmful to man. The novel compounds are distinguished by excellent activity at low rates of application, by being well tolerated by plants and by being environmentally safe. They have very useful curative, preventive and systemic properties and may be used for protecting numerous cultivated plants. The compounds of formula (I) can be used to inhibit or destroy the pests that occur on plants or parts of plants (fruit, blossoms, leaves, stems, tubers, roots) of different crops of useful plants, while at the same time protecting also those parts of the plants that grow later, e.g., from phytopathogenic microorganisms.

The present invention further relates to a method for controlling or preventing infestation of plants or plant propagation material and/or harvested food crops susceptible to microbial attack by treating plants or plant propagation material and/or harvested food crops wherein an effective amount a compound of formula (I) is applied to the plants, to parts thereof or the locus thereof.

It is also possible to use the compounds of formula (I) as fungicide. The term "fungicide" as used herein means a compound that controls, modifies, or prevents the growth of fungi. The term "fungicidally effective amount" means the quantity of such a compound or combination of such compounds that is capable of producing an effect on the growth of fungi. Controlling or modifying effects include all deviation from natural development, such as killing, retardation and the like, and prevention includes barrier or other defensive formation in or on a plant to prevent fungal infection.

It is also possible to use compounds of formula (I) as dressing agents for the treatment of plant propagation material, e.g., seed, such as fruits, tubers or grains, or plant cuttings (e.g., rice), for the protection against fungal infections, as well as against phytopathogenic fungi occurring in the soil. The propagation material can be treated with a composition comprising a compound of formula (I) before planting: seed, e.g., can be dressed before being sown.

The active ingredients according to the invention can also be applied to grains (coating), either by impregnating the seeds in a liquid formulation or by coating them with a solid formulation. The composition can also be applied to the planting site when the propagation material is being planted, e.g., to the seed furrow during sowing. The invention relates also to such methods of treating plant propagation material and to the plant propagation material so treated.

Furthermore, the compounds according to present invention can be used for controlling fungi in related areas, for example in the protection of technical materials, including wood and wood related technical products, in food storage, in hygiene management.

In addition, the invention could be used to protect non-living materials from fungal attack, e.g., lumber, wall boards and paint.

The compounds of formula (I) may be, for example, effective against fungi and fungal vectors of disease as well as phytopathogenic bacteria) and viruses. These fungi and fungal vectors of disease as well as phytopathogenic bacteria and viruses are for example: *Absidia corymbifera, Alternaria* spp, *Aphanomyces* spp, *Ascochyta* spp, *Aspergillus* spp. including *A. flavus, A. fumigatus, A. nidulans, A. niger, A. terrus, Aureobasidium* spp. including *A. pullulans, Blastomyces dermatitidis, Blumeria graminis, Bremia lactucae,*

*Botryosphaeria* spp. including *B. dothidea, B. obtusa, Botrytis* spp. inclusing *B. cinerea, Candida* spp. including *C. albicans, C. glabrata, C. krusei, C. lusitaniae, C. parapsilosis, C. tropicalis, Cephaloascus fragrans, Ceratocystis* spp, *Cercospora* spp. including *C. arachidicola, Cercosporidium personatum, Cladosporium* spp, *Claviceps purpurea, Coccidioides immitis, Cochliobolus* spp, *Colletotrichum* spp. including *C. musae, Cryptococcus neoformans, Diaporthe* spp, *Didymella* spp, *Drechslera* spp, *Elsinoe* spp, *Epidermophyton* spp, *Erwinia amylovora, Erysiphe* spp. including *E. cichoracearum, Eutypa lata, Fusarium* spp. including *F. culmorum, F. graminearum, F. langsethiae, F. moniliforme, F. oxysporum, F. proliferatum, F. subglutinans, F. solani, Gaeumannomyces graminis, Gibberella fujikuroi, Gloeodes pomigena, Gloeosporium musarum, Glomerella cingulate, Guignardia bidwellii, Gymnosporangium juniperi-virginianae, Helminthosporium* spp, *Hemileia* spp, *Histoplasma* spp. including *H. capsulatum, Laetisaria fuciformis, Leptographium lindbergi, Leveillula taurica, Lophodermium seditiosum, Microdochium nivale, Microsporum* spp, *Monilinia* spp, *Mucor* spp, *Mycosphaerella* spp. including *M. graminicola, M. pomi, Oncobasidium theobromaeon, Ophiostoma piceae, Paracoccidioides* spp, *Penicillium* spp. including *P. digitatum, P. italicum, Petriellidium* spp, *Peronosclerospora* spp. Including *P. maydis, P. philippinensis* and *P. sorghi, Peronospora* spp, *Phaeosphaeria nodorum, Phakopsora pachyrhizi, Phellinus igniarus, Phialophora* spp, *Phoma* spp, *Phomopsis viticola, Phytophthora* spp. including *P. infestans, Plasmopara* spp. including *P. halstedii, P. viticola, Pleospora* spp., *Podosphaera* spp. including *P. leucotricha, Polymyxa graminis, Polymyxa betae, Pseudocercosporella herpotrichoides, Pseudomonas* spp, *Pseudoperonospora* spp. including *P. cubensis, P. humuli, Pseudopeziza tracheiphila, Puccinia* Spp. including *P. hordei, P. recondita, P. striiformis, P. triticina, Pyrenopeziza* spp, *Pyrenophora* spp, *Pyricularia* spp. including *P. oryzae, Pythium* spp. including *P. ultimum, Ramularia* spp, *Rhizoctonia* spp, *Rhizomucor pusillus, Rhizopus arrhizus, Rhynchosporium* spp, *Scedosporium* spp. including *S. apiospermum* and *S. prolificans, Schizothyrium pomi, Sclerotinia* spp, *Sclerotium* spp, *Septoria* spp, including *S. nodorum, S. tritici, Sphaerotheca macularis, Sphaerotheca fusca* (*Sphaerotheca fuliginea*), *Sporothorix* spp, *Stagonospora nodorum, Stemphylium* spp., *Stereum hirsutum, Thanatephorus cucumeris, Thielaviopsis basicola, Tilletia* spp, *Trichoderma* spp., including *T. harzianum, T. pseudokoningii, T. viride, Trichophyton* spp, *Typhula* spp, *Uncinula necator, Urocystis* spp, *Ustilago* spp, *Venturia* spp. including *V. inaequalis, Verticillium* spp, and *Xanthomonas* spp.

Within the scope of present invention, target crops and/or useful plants to be protected typically comprise perennial and annual crops, such as berry plants for example blackberries, blueberries, cranberries, raspberries and strawberries; cereals for example barley, maize (corn), millet, oats, rice, rye, sorghum triticale and wheat; fibre plants for example cotton, flax, hemp, jute and sisal; field crops for example sugar and fodder beet, coffee, hops, mustard, oilseed rape (canola), poppy, sugar cane, sunflower, tea and tobacco; fruit trees for example apple, apricot, avocado, banana, cherry, citrus, nectarine, peach, pear and plum; grasses for example Bermuda grass, bluegrass, bentgrass, centipede grass, fescue, ryegrass, St. Augustine grass and *Zoysia* grass; herbs such as basil, borage, chives, coriander, lavender, lovage, mint, oregano, parsley, rosemary, sage and thyme; legumes for example beans, lentils, peas and soya beans; nuts for example almond, cashew, ground nut, hazelnut, peanut, pecan, pistachio and walnut; palms for example oil palm; ornamentals for example flowers, shrubs and trees; other trees, for example cacao, coconut, olive and rubber; vegetables for example asparagus, aubergine, broccoli, cabbage, carrot, cucumber, garlic, lettuce, marrow, melon, okra, onion, pepper, potato, pumpkin, rhubarb, spinach and tomato; and vines for example grapes.

The term "useful plants" is to be understood as including also useful plants that have been rendered tolerant to herbicides like bromoxynil or classes of herbicides (such as, for example, HPPD inhibitors, ALS inhibitors, for example primisulfuron, prosulfuron and trifloxysulfuron, EPSPS (5-enol-pyrovyl-shikimate-3-phosphate-synthase) inhibitors, GS (glutamine synthetase) inhibitors or PPO (protoporphyrinogen-oxidase) inhibitors) as a result of conventional methods of breeding or genetic engineering. An example of a crop that has been rendered tolerant to imidazolinones, e.g. imazamox, by conventional methods of breeding (mutagenesis) is Clearfield® summer rape (Canola). Examples of crops that have been rendered tolerant to herbicides or classes of herbicides by genetic engineering methods include glyphosate- and glufosinate-resistant maize varieties commercially available under the trade names RoundupReady®, Herculex I® and LibertyLink®.

The term "useful plants" is to be understood as including also useful plants which have been so transformed by the use of recombinant DNA techniques that they are capable of synthesising one or more selectively acting toxins, such as are known, for example, from toxin-producing bacteria, especially those of the genus *Bacillus*.

Examples of such plants are: YieldGard® (maize variety that expresses a Cry(IA)(b) toxin); YieldGard Rootworm® (maize variety that expresses a CryIIIB(b1) toxin); YieldGard Plus® (maize variety that expresses a Cry(IA)(b) and a CryIIIB(b1) toxin); Starlink® (maize variety that expresses a Cry9(c) toxin); Herculex 1® (maize variety that expresses a CryIF(a2) toxin and the enzyme phosphinothricine N-acetyltransferase (PAT) to achieve tolerance to the herbicide glufosinate ammonium); NuCOTN 33B® (cotton variety that expresses a Cry(IA)(c) toxin); Bollgard I® (cotton variety that expresses a Cry(IA)(c) toxin); Bollgard II® (cotton variety that expresses a Cry(IA)(c) and a CryI (IA)(b) toxin); VIPCOT® (cotton variety that expresses a VIP toxin); NewLeaf® (potato variety that expresses a CryII(IA) toxin); NatureGard® Agrisure® GT Advantage (GA21 glyphosate-tolerant trait), Agrisure® CB Advantage (Bt11 corn borer (CB) trait), Agrisure® RW (corn rootworm trait) and Protecta®.

The term "crops" is to be understood as including also crop plants which have been so transformed by the use of recombinant DNA techniques that they are capable of synthesising one or more selectively acting toxins, such as are known, for example, from toxin-producing bacteria, especially those of the genus *Bacillus*.

Toxins that can be expressed by such transgenic plants include, for example, insecticidal proteins from *Bacillus cereus* or *Bacillus popilliae*; or insecticidal proteins from *Bacillus thuringiensis*, such as 6-endotoxins, e.g. Cry1Ab, Cry1Ac, Cry1F, Cry1Fa2, Cry2Ab, Cry3A, Cry3Bb1 or Cry9C, or vegetative insecticidal proteins (Vip), e.g. Vip1, Vip2, Vip3 or Vip3A; or insecticidal proteins of bacteria colonising nematodes, for example *Photorhabdus* spp. or *Xenorhabdus* spp., such as *Photorhabdus luminescens, Xenorhabdus nematophilus*; toxins produced by animals, such as scorpion toxins, arachnid toxins, wasp toxins and other insect-specific neurotoxins; toxins produced by fungi, such as Streptomycetes toxins, plant lectins, such as pea lectins, barley lectins or snowdrop lectins; agglutinins; proteinase inhibitors, such as trypsin inhibitors, serine protease inhibitors, patatin, cystatin, papain inhibitors; ribosome-inactivating proteins (RIP), such as ricin, maize-RIP, abrin, luffin, saporin or bryodin; steroid metabolism enzymes, such as 3-hydroxysteroidoxidase, ecdysteroid-UDP-glycosyl-transferase, cholesterol oxidases, ecdysone inhibitors, HMG-COA-reductase, ion channel blockers, such as blockers of sodium or calcium channels, juvenile hormone esterase, diuretic hormone receptors, stilbene synthase, bibenzyl synthase, chitinases and glucanases.

In the context of the present invention there are to be understood by 6-endotoxins, for example Cry1Ab, Cry1Ac, Cry1F, Cry1Fa2, Cry2Ab, Cry3A, Cry3Bb1 or Cry9C, or vegetative insecticidal proteins (Vip), for example Vip1, Vip2, Vip3 or Vip3A, expressly also hybrid toxins, truncated toxins and modified toxins. Hybrid toxins are produced recombinantly by a new combination of different domains of those proteins (see, for example, WO 02/15701). Truncated toxins, for example a truncated Cry1Ab, are known. In the case of modified toxins, one or more amino acids of the naturally occurring toxin are replaced. In such amino acid replacements, preferably non-naturally present protease recognition sequences are inserted into the toxin, such as, for example, in the case of Cry3A055, a cathepsin-G-recognition sequence is inserted into a Cry3A toxin (see WO 03/018810).

Examples of such toxins or transgenic plants capable of synthesising such toxins are disclosed, for example, in EP-A-0 374 753, WO 93/07278, WO 95/34656, EP-A-0 427 529, EP-A-451 878 and WO 03/052073. The processes for the preparation of such transgenic plants are generally known to the person skilled in the art and are described, for example, in the publications mentioned above. CryI-type deoxyribonucleic acids and their preparation are known, for example, from WO 95/34656, EP-A-0 367 474, EP-A-0 401 979 and WO 90/13651.

The toxin contained in the transgenic plants imparts to the plants tolerance to harmful insects. Such insects can occur in any taxonomic group of insects, but are especially commonly found in the beetles (Coleoptera), two-winged insects (Diptera) and butterflies (Lepidoptera).

Transgenic plants containing one or more genes that code for an insecticidal resistance and express one or more toxins are known and some of them are commercially available. Examples of such plants are: YieldGard® (maize variety that expresses a Cry1Ab toxin); YieldGard Rootworm® (maize variety that expresses a Cry3Bb1 toxin); YieldGard Plus® (maize variety that expresses a Cry1Ab and a Cry3Bb1 toxin); Starlink® (maize variety that expresses a Cry9C toxin); Herculex 1® (maize variety that expresses a Cry1Fa2 toxin and the enzyme phosphinothricine N-acetyltransferase (PAT) to achieve tolerance to the herbicide glufosinate ammonium); NuCOTN 33B® (cotton variety that expresses a Cry1Ac toxin); Bollgard I® (cotton variety that expresses a Cry1Ac toxin); Bollgard 11® (cotton variety that expresses a Cry1Ac and a Cry2Ab toxin); VipCot® (cotton variety that expresses a Vip3A and a Cry1Ab toxin); NewLeaf® (potato variety that expresses a Cry3A toxin); NatureGard®, Agrisure® GT Advantage (GA21 glyphosate-tolerant trait), Agrisure® CB Advantage (Bt11 corn borer (CB) trait) and Protecta®.

Further examples of such transgenic crops are:

1. Bt11 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and Sesamia nonagrioides) by transgenic expression of a truncated Cry1Ab toxin. Bt11 maize also transgenically expresses the enzyme PAT to achieve tolerance to the herbicide glufosinate ammonium.
2. Bt176 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and Sesamia nonagrioides) by transgenic expression of a Cry1Ab toxin. Bt176 maize also transgenically expresses the enzyme PAT to achieve tolerance to the herbicide glufosinate ammonium.
3. MIR604 Maize from Syngenta Seeds SAS, Chemin de l'Hobit 27, F-31 790 St. Sauveur, France, registration number C/FR/96/05/10. Maize which has been rendered insect-resistant by transgenic expression of a modified Cry3A toxin. This toxin is Cry3A055 modified by insertion of a cathepsin-G-protease recognition sequence. The preparation of such transgenic maize plants is described in WO 03/018810.
4. MON 863 Maize from Monsanto Europe S.A. 270-272 Avenue de Tervuren, B-1150 Brussels, Belgium, registration number C/DE/02/9. MON 863 expresses a Cry3Bb1 toxin and has resistance to certain Coleoptera insects.
5. IPC 531 Cotton from Monsanto Europe S.A. 270-272 Avenue de Tervuren, B-1150 Brussels, Belgium, registration number C/ES/96/02.
6. 1507 Maize from Pioneer Overseas Corporation, Avenue Tedesco, 7 B-1160 Brussels, Belgium, registration number C/NL/00/10. Genetically modified maize for the expression of the protein Cry1F for achieving resistance to certain Lepidoptera insects and of the PAT protein for achieving tolerance to the herbicide glufosinate ammonium.
7. NK603×MON 810 Maize from Monsanto Europe S.A. 270-272 Avenue de Tervuren, B-1150 Brussels, Belgium, registration number C/GB/02/M3/03. Consists of conventionally bred hybrid maize varieties by crossing the genetically modified varieties NK603 and MON 810. NK603×MON 810 Maize transgenically expresses the protein CP4 EPSPS, obtained from *Agrobacterium* sp. strain CP4, which imparts tolerance to the herbicide Roundup® (contains glyphosate), and also a Cry1Ab toxin obtained from *Bacillus thuringiensis* subsp. kurstaki which brings about tolerance to certain Lepidoptera, include the European corn borer.

Additionally, to date, no cross-resistance has been observed between the compounds of Formula (I) (including any one of compounds described in Table 2 (below)) and any fungicidal solutions used to control phytopathogenic fungi such as *Absidia corymbifera, Alternaria* spp, *Aphanomyces* spp, *Ascochyta* spp, *Aspergillus* spp. including *A. flavus, A. fumigatus, A. nidulans, A. niger, A. terrus, Aureobasidium* spp. including *A. pullulans, Blastomyces dermatitidis, Blumeria graminis, Bremia lactucae, Botryosphaeria* spp. including *B. dothidea, B. obtusa, Botrytis* spp. inclusing *B. cinerea, Candida* spp. including *C. albicans, C. glabrata, C. krusei, C. lusitaniae, C. parapsilosis, C. tropicalis, Cephaloascus fragrans, Ceratocystis* spp, *Cercospora* spp. including *C. arachidicola, Cercosporidium personatum, Cladosporium* spp, *Claviceps purpurea, Coccidioides immitis, Cochliobolus* spp, *Colletotrichum* spp. including *C. musae, Cryptococcus neoformans, Diaporthe* spp, *Didymella* spp, *Drechslera* spp, *Elsinoe* spp, *Epidermophyton* spp, *Erwinia amylovora, Erysiphe* spp. including *E. cichoracearum,*

*Eutypa lata, Fusarium* spp. including *F. culmorum, F. graminearum, F. langsethiae, F. moniliforme, F. oxysporum, F. proliferatum, F. subglutinans, F. solani, Gaeumannomyces graminis, Gibberella fujikuroi, Gloeodes pomigena, Gloeosporium musarum, Glomerella cingulate, Guignardia bidwellii, Gymnosporangium juniperi-virginianae, Helminthosporium* spp, *Hemileia* spp, *Histoplasma* spp. including *H. capsulatum, Laetisaria fuciformis, Leptographium lindbergi, Leveillula taurica, Lophodermium seditiosum, Microdochium nivale, Microsporum* spp, *Monilinia* spp, *Mucor* spp, *Mycosphaerella* spp. including *M. graminicola, M. pomi, Oncobasidium theobromaeon, Ophiostoma piceae, Paracoccidioides* spp, *Penicillium* spp. including *P. digitatum, P. italicum, Petriellidium* spp, *Peronosclerospora* spp. Including *P. maydis, P. philippinensis* and *P. sorghi, Peronospora* spp, *Phaeosphaeria nodorum, Phakopsora pachyrhizi, Phellinus igniarus, Phialophora* spp, *Phoma* spp, *Phomopsis viticola, Phytophthora* spp. including *P. infestans, Plasmopara* spp. including *P. halstedii, P. viticola, Pleospora* spp., *Podosphaera* spp. including *P. leucotricha, Polymyxa graminis, Polymyxa betae, Pseudocercosporella herpotrichoides, Pseudomonas* spp, *Pseudoperonospora* spp. including *P. cubensis, P. humuli, Pseudopeziza tracheiphila, Puccinia* Spp. including *P. hordei, P. recondita, P. striiformis, P. triticina, Pyrenopeziza* spp, *Pyrenophora* spp, *Pyricularia* spp. including *P. oryzae, Pythium* spp. including *P. ultimum, Ramularia* spp, *Rhizoctonia* spp, *Rhizomucor pusillus, Rhizopus arrhizus, Rhynchosporium* spp, *Scedosporium* spp. including *S. apiospermum* and *S. prolificans, Schizothyrium pomi, Sclerotinia* spp, *Sclerotium* spp, *Septoria* spp, including *S. nodorum, S. tritici, Sphaerotheca macularis, Sphaerotheca fusca* (*Sphaerotheca fuliginea*), *Sporothorix* spp, *Stagonospora nodorum, Stemphylium* spp., *Stereum hirsutum, Thanatephorus cucumeris, Thielaviopsis basicola, Tilletia* spp, *Trichoderma* spp., including *T. harzianum, T. pseudokoningii, T. viride, Trichophyton* spp, *Typhula* spp, *Uncinula necator, Urocystis* spp, *Ustilago* spp, *Venturia* spp. including *V. inaequalis, Verticillium* spp, and *Xanthomonas* spp., in particular, *Zymoseptoria tritici, Puccinia recondita, Puccinia striiformis, Erysiphe graminis, Uncinula necator, Sphaerotheca fuliginea, Leveillula taurica, Phakopsora pachyrhizi, Pyricularia oryzae, Alternaria solani, Alternaria alternata, Mycosphaerella fijiensis, Colletotrichum lagenarium, Didymella bryoniae, Ascochyta pisii, Verticillium dahliae, Pyrenophora teres, Cercospora beticola, Ramularia collo-cygni, Botrytis cinerea, Sclerotinia sclerotiorum, Monilinia laxa, Monographaella nivalis* and *Venturia inaequalis.*

Indeed, fungicidal-resistant strains in any of the species as outlined above have been reported in the scientific literature, with strains resistant to one or more fungicides from at least one of the following fungicidal mode of action classes: quinone-outside-inhibitors (QoI), quinone-inside-inhibitors (QiI), succinate dehydrogenase inhibitors (SDHI) and sterol demethylation-inhibitors (DMI). Such fungicidal-resistant strains may contain:

A mutation in the mitochondrial cytochrome b gene conferring resistance to Qo inhibitors, wherein the mutation is G143A, F129L or G137R. See for example: Gisi et al., Pest Manag Sci 56, 833-841, (2000), Lucas, Pestic Outlook 14(6), 268-70 (2003), Fraaije et al., Phytopathol 95(8), 933-41 (2005), Sierotzki et al., Pest Manag Sci 63(3), 225-233 (2007), Semar et al., Journal of Plant Diseases and Protection (3), 117-119 (2007); and Pasche et al., Crop Protection 27(3-5), 427-435 (2008).

A mutation in the mitochondrial cytochrome b gene conferring resistance to Qi inhibitors, wherein the mutation is G37A/C/D/S/V. See for example: Meunier et al., Pest Manag Sci 2019; 75: 2107-2114.

A mutation in the genes encoding the SdhB,C,D subunits conferring resistance to SDHI inhibitors wherein the mutation is in the following major pathogens:

*Botrytis cinerea*: B-P225H/L/T/Y/F, B-N2301, B-H272L/Y/R, C-P80H/L, C-N87S;

*Alternaria solani*: B-H278R/Y, C-H134R/Q, D-D123E, D-H133R and C-H134R;

*Zymoseptoria tritici*: sdhB: N225T, N2251, R265P, T2681, T268A. In sdhC: T79N, T791, W80S, W80A, A84F, N86S, N86A, P127A, R151 M/S/T/G, R151S, R151T, H152R/Y, V166M, T168R. In sdhD: 150F, M114V, D129G, T20P+K186R;

*Pyrenophora teres*: In sdhB: S66P, N2351, H277Y. In sdhC: K49E, R64K, N75S, G79R, H134R, S135R. In sdhD: D124E, H134R, G138V, D145G;

*Ramularia collo-cygni*: In sdhB: N224T, T2671. In sdhC: N87S, G91R, H146R/L, G171D, H153R;

*Phakopsora pachyrhizi*: C-186F;

*Sclerotinia sclerotiorum*: In sdhB: H273Y. In sdhC: G91R, H146R. In sdhD: T108K, H132R, G150R.

Major source of information is www.frac.info, Sierotzki and Scalliet Phytopathology (2013) 103(9): 880-887 and Simóes et al., *J Plant Dis Prot* (2018) 125: 21-2.

A mutation or combination of mutations in the CYP51 gene conferring resistance to DMI inhibitors wherein the mutations are: L50S, D134G, V136A/C, Y137F, S188N, A379G, 1381V, deletion 459-460, Y461H/S, N513K, S524T. Major source of information is www.frac.info, Cools et al., Plant Pathol (2013) 62: 36-42 and Schmitz H K et al., Pest Manag Sci (2014) 70: 378-388.

Thus, in a preferred embodiment, the compounds of Formula (I) (including any one of compounds described in Table 2 (below)), or fungicidal compositions according to the present invention comprising a compound of Formula (I), are used to control fungal strains which are resistant to one or more fungicides from any of the following fungicidal MoA classes: quinone-outside-inhibitors (QoI), quinone-inside-inhibitors (QiI), succinate dehydrogenase inhibitors (SDHI) and sterol demethylation-inhibitors (DMI).

The term "locus" as used herein means fields in or on which plants are growing, or where seeds of cultivated plants are sown, or where seed will be placed into the soil. It includes soil, seeds, and seedlings, as well as established vegetation.

The term "plants" refers to all physical parts of a plant, including seeds, seedlings, saplings, roots, tubers, stems, stalks, foliage, and fruits.

The term "plant propagation material" is understood to denote generative parts of the plant, such as seeds, which can be used for the multiplication of the latter, and vegetative material, such as cuttings or tubers, for example potatoes. There may be mentioned for example seeds (in the strict sense), roots, fruits, tubers, bulbs, rhizomes and parts of plants. Germinated plants and young plants which are to be transplanted after germination or after emergence from the soil, may also be mentioned. These young plants may be protected before transplantation by a total or partial treatment by immersion. Preferably "plant propagation material" is understood to denote seeds.

Pesticidal agents referred to herein using their common name are known, for example, from "The Pesticide Manual", 15th Ed., British Crop Protection Council 2009.

The compounds of formula (I) may be used in unmodified form or, preferably, together with the adjuvants conventionally employed in the art of formulation. To this end, they may be conveniently formulated in known manner to emulsifiable concentrates, coatable pastes, directly sprayable or dilutable solutions or suspensions, dilute emulsions, wettable powders, soluble powders, dusts, granulates, and also encapsulations e.g. in polymeric substances. As with the type of the compositions, the methods of application, such as spraying, atomising, dusting, scattering, coating or pouring, are chosen in accordance with the intended objectives and the prevailing circumstances. The compositions may also contain further adjuvants such as stabilizers, antifoams, viscosity regulators, binders or tackifiers as well as fertilizers, micronutrient donors or other formulations for obtaining special effects.

Suitable carriers and adjuvants, e.g., for agricultural use, can be solid or liquid and are substances useful in formulation technology, e.g. natural or regenerated mineral substances, solvents, dispersants, wetting agents, tackifiers, thickeners, binders or fertilizers. Such carriers are for example described in WO 97/33890.

The compounds of formula (I) are normally used in the form of compositions and can be applied to the crop area or plant to be treated, simultaneously or in succession with further compounds. These further compounds can be, e.g., fertilizers or micronutrient donors or other preparations, which influence the growth of plants. They can also be selective herbicides or non-selective herbicides as well as insecticides, fungicides, bactericides, nematicides, molluscicides or mixtures of several of these preparations, if desired together with further carriers, surfactants or application promoting adjuvants customarily employed in the art of formulation.

The compounds of formula (I) may be used in the form of (fungicidal) compositions for controlling or protecting against phytopathogenic microorganisms, comprising as active ingredient at least one compound of formula (I) or of at least one preferred individual compound as above-defined, in free form or in agrochemically usable salt form, and at least one of the above-mentioned adjuvants.

The invention provides a composition, preferably a fungicidal composition, comprising at least one compound formula (I) an agriculturally acceptable carrier and optionally an adjuvant. An agricultural acceptable carrier is for example a carrier that is suitable for agricultural use. Agricultural carriers are well known in the art. Preferably, said composition may comprise at least one or more pesticidally active compounds, for example an additional fungicidal active ingredient in addition to the compound of formula (I).

The compound of formula (I) may be the sole active ingredient of a composition or it may be admixed with one or more additional active ingredients such as a pesticide, fungicide, synergist, herbicide or plant growth regulator where appropriate. An additional active ingredient may, in some cases, result in unexpected synergistic activities.

Examples of suitable additional active ingredients include the following acycloamino acid fungicides, aliphatic nitrogen fungicides, amide fungicides, anilide fungicides, antibiotic fungicides, aromatic fungicides, arsenical fungicides, aryl phenyl ketone fungicides, benzamide fungicides, benzanilide fungicides, benzimidazole fungicides, benzothiazole fungicides, botanical fungicides, bridged diphenyl fungicides, carbamate fungicides, carbanilate fungicides, conazole fungicides, copper fungicides, dicarboximide fungicides, dinitrophenol fungicides, dithiocarbamate fungicides, dithiolane fungicides, furamide fungicides, furanilide fungicides, hydrazide fungicides, imidazole fungicides, mercury fungicides, morpholine fungicides, organophosphorous fungicides, organotin fungicides, oxathiin fungicides, oxazole fungicides, phenylsulfamide fungicides, polysulfide fungicides, pyrazole fungicides, pyridine fungicides, pyrimidine fungicides, pyrrole fungicides, quaternary ammonium fungicides, quinoline fungicides, quinone fungicides, quinoxaline fungicides, strobilurin fungicides, sulfonanilide fungicides, thiadiazole fungicides, thiazole fungicides, thiazolidine fungicides, thiocarbamate fungicides, thiophene fungicides, triazine fungicides, triazole fungicides, triazolopyrimidine fungicides, urea fungicides, valinamide fungicides, and zinc fungicides.

Examples of suitable additional active ingredients also include the following: petroleum oils, 1,1-bis(4-chlorophenyl)-2-ethoxyethanol, 2,4-dichlorophenyl benzenesulfonate, 2-fluoro-N-methyl-N-1-naphthylacetamide, 4-chlorophenyl phenyl sulfone, acetoprole, aldoxycarb, amidithion, amidothioate, amiton, amiton hydrogen oxalate, amitraz, aramite, arsenous oxide, azobenzene, azothoate, benomyl, benoxafos, benzyl benzoate, bixafen, brofenvalerate, bromocyclen, bromophos, bromopropylate, buprofezin, butocarboxim, butoxycarboxim, butylpyridaben, calcium polysulfide, camphechlor, carbanolate, carbophenothion, cymiazole, chinomethionat, chlorbenside, chlordimeform, chlordimeform hydrochloride, chlorfenethol, chlorfenson, chlorfensulfide, chlorobenzilate, chloromebuform, chloromethiuron, chloropropylate, chlorthiophos, cinerin I, cinerin II, cinerins, closantel, coumaphos, crotamiton, crotoxyphos, cufraneb, cyanthoate, DCPM, DDT, demephion, demephion-O, demephion-S, demeton-methyl, demeton-O, demeton-O-methyl, demeton-S, demeton-S-methyl, demeton-S-methylsulfon, dichlofluanid, dichlorvos, dicliphos, dienochlor, dimefox, dinex, dinex-diclexine, dinocap-4, dinocap-6, dinocton, dinopenton, dinosulfon, dinoterbon, dioxathion, diphenyl sulfone, disulfiram, DNOC, dofenapyn, doramectin, endothion, eprinomectin, ethoate-methyl, etrimfos, fenazaflor, fenbutatin oxide, fenothiocarb, fenpyrad, fenpyroximate, fenpyrazamine, fenson, fentrifanil, flubenzimine, flucycloxuron, fluenetil, fluorbenside, FMC 1137, formetanate, formetanate hydrochloride, formparanate, gamma-HCH, glyodin, halfenprox, hexadecyl cyclopropanecarboxylate, isocarbophos, jasmolin I, jasmolin II, jodfenphos, lindane, malonoben, mecarbam, mephosfolan, mesulfen, methacrifos, methyl bromide, metolcarb, mexacarbate, milbemycin oxime, mipafox, monocrotophos, morphothion, moxidectin, naled, 4-chloro-2-(2-chloro-2-methyl-propyl)-5-[(6-iodo-3-pyridyl)methoxy]pyridazin-3-one, nifluridide, nikkomycins, nitrilacarb, nitrilacarb 1:1 zinc chloride complex, omethoate, oxydeprofos, oxydisulfoton, pp'-DDT, parathion, permethrin, phenkapton, phosalone, phosfolan, phosphamidon, polychloroterpenes, polynactins, proclonol, promacyl, propoxur, prothidathion, prothoate, pyrethrin I, pyrethrin II, pyrethrins, pyridaphenthion, pyrimitate, quinalphos, quintiofos, R-1492, phosglycin, rotenone, schradan, sebufos, selamectin, sophamide, SSI-121, sulfiram, sulfluramid, sulfotep, sulfur, diflovidazin, tau-fluvalinate, TEPP, terbam, tetradifon, tetrasul, thiafenox, thiocarboxime, thiofanox, thiometon, thioquinox, thuringiensin, triamiphos, triarathene, triazophos, triazuron, trifenofos, trinactin, vamidothion, vaniliprole, bethoxazin, copper dioctanoate, copper sulfate, cybutryne, dichlone, dichlorophen, endothal, fentin, hydrated lime, nabam, quinoclamine, quinonamid, simazine, triphenyltin acetate, triphenyltin hydroxide, crufomate, piperazine, thiophanate, chloralose, fenthion, pyridin-4-amine, strychnine, 1-hydroxy-1H-pyridine-2-thione, 4-(quinoxalin-2-ylamino)benzenesulfonamide, 8-hydroxyquinoline sulfate, bronopol, copper hydroxide, cresol, dipyrithione, dodicin, fenaminosulf, formaldehyde, hydrargaphen, kasugamycin, kasugamycin hydrochloride hydrate, nickel bis(dimethyldithiocarbamate), nitrapyrin, octhilinone, oxolinic acid, oxytetracycline, potassium hydroxyquinoline sulfate, probenazole, streptomycin, streptomycin sesquisulfate, tecloftalam, thiomersal, *Adoxophyes orana* GV, *Agrobacterium radiobacter, Amblyseius* spp., *Anagrapha falcifera* NPV, Anagrus *atomus, Aphelinus abdominalis, Aphidius colemani, Aphidoletes aphidimyza, Autographa californica* NPV, *Bacillus sphaericus* Neide, *Beauveria brongniartii, Chrysoperla carnea, Cryptolaemus montrouzieri, Cydia pomonella* GV, *Dacnusa sibirica, Diglyphus isaea, Encarsia formosa, Eretmocerus eremicus, Heterorhabditis bacteriophora* and *H. megidis, Hippodamia convergens, Leptomastix dactylopii, Macrolophus caliginosus, Mamestra brassicae* NPV, *Metaphycus helvolus, Metarhizium anisopliae* var. *acridum, Metarhizium anisopliae* var. *anisopliae, Neodiprion sertifer* NPV and *N. lecontei* NPV, *Orius* spp., *Paecilomyces fumosoroseus, Phytoseiulus persimilis, Steinernema bibionis, Steinernema carpocapsae, Steinernema feltiae, Steinernema glaseri, Steinernema riobrave, Steinernema riobravis, Steinernema scapterisci, Steinernema* spp., *Trichogramma* spp., *Typhlodromus occidentalis, Verticillium lecanii*, apholate, bisazir, busulfan, dimatif, hemel, hempa, metepa, methiotepa, methyl apholate, morzid, penfluron, tepa, thiohempa, thiotepa, tretamine, uredepa, (E)-dec-5-en-1-yl acetate with (E)-dec-5-en-1-ol, (E)-tridec-4-en-1-yl acetate, (E)-6-methylhept-2-en-4-ol, (E,Z)-tetradeca-4,10-dien-1-yl acetate, (Z)-dodec-7-en-1-yl acetate, (Z)-hexadec-11-enal, (Z)-hexadec-11-en-1-yl acetate, (Z)-hexadec-13-en-11-yn-1-yl acetate, (Z)-icos-13-en-10-one, (Z)-tetradec-7-en-1-al, (Z)-tetradec-9-en-1-ol, (Z)-tetradec-9-en-1-yl acetate, (7E,9Z)-dodeca-7,9-dien-1-yl acetate, (9Z,11E)-tetradeca-9,11-dien-1-yl acetate, (9Z,12E)-tetradeca-9,12-dien-1-yl acetate, 14-methyloctadec-1-ene, 4-methylnonan-5-ol with 4-methylnonan-5-one, alpha-multistriatin, brevicomin, codlelure, codlemone, cuelure, disparlure, dodec-8-en-1-yl acetate, dodec-9-en-1-yl acetate, dodeca-8, 10-dien-1-yl acetate, dominicalure, ethyl 4-methyloctanoate, eugenol, frontalin, grandlure, grandlure I, grandlure II, grandlure III, grandlure IV, hexalure, ipsdienol, ipsenol, japonilure, lineatin, litlure, looplure, medlure, megatomoic acid, methyl eugenol, muscalure, octadeca-2,13-dien-1-yl acetate, octadeca-3,13-dien-1-yl acetate, orfralure, oryctalure, ostramone, siglure, sordidin, sulcatol, tetradec-11-en-1-yl acetate, trimedlure, trimedlure A, trimedlure $B_1$, trimedlure $B_2$, trimedlure C, trunc-call, 2-(octylthio)-ethanol, butopyronoxyl, butoxy(polypropylene glycol), dibutyl adipate, dibutyl phthalate, dibutyl succinate, diethyltoluamide, dimethyl carbate, dimethyl phthalate, ethyl hexanediol, hexamide, methoquin-butyl, methylneodecanamide, oxamate, picaridin, 1-dichloro-1-nitroethane, 1,1-dichloro-2,2-bis(4-ethylphenyl)ethane, 1,2-dichloropropane with 1,3-dichloropropene, 1-bromo-2-chloroethane, 2,2,2-trichloro-1-(3,4-dichlorophenyl)ethyl acetate, 2,2-dichlorovinyl 2-ethylsulfinylethyl methyl phosphate, 2-(1,3-dithiolan-2-yl)phenyl dimethylcarbamate, 2-(2-butoxyethoxy)ethyl thiocyanate, 2-(4,5-dimethyl-1,3-dioxolan-2-yl)phenyl methylcarbamate, 2-(4-chloro-3,5-xylyloxy) ethanol, 2-chlorovinyl diethyl phosphate, 2-imidazolidone, 2-isovalerylindan-1,3-dione, 2-methyl(prop-2-ynyl)aminophenyl methylcarbamate, 2-thiocyanatoethyl laurate, 3-bromo-1-chloroprop-1-ene, 3-methyl-1-phenylpyrazol-5-yl dimethylcarbamate, 4-methyl(prop-2-ynyl)amino-3,5-xylyl methylcarbamate, 5,5-dimethyl-3-oxocyclohex-1-enyl dimethylcarbamate, acethion, acrylonitrile, aldrin, allosamidin, allyxycarb, alpha-ecdysone, aluminium phosphide, aminocarb, anabasine, athidathion, azamethiphos, *Bacillus thuringiensis* delta endotoxins, barium hexafluorosilicate, barium polysulfide, barthrin, Bayer 22/190, Bayer 22408, beta-cyfluthrin, beta-cypermethrin, bioethanomethrin, biopermethrin, bis(2-chloroethyl) ether, borax, bromfenvinfos, bromo-DDT, bufencarb, butacarb, butathiofos, butonate, calcium arsenate, calcium cyanide, carbon disulfide, carbon tetrachloride, cartap hydrochloride, cevadine, chlorbicyclen, chlordane, chlordecone, chloroform, chloropicrin, chlorphoxim, chlorprazophos, cis-resmethrin, cismethrin, clocythrin, copper acetoarsenite, copper arsenate, copper oleate, coumithoate, cryolite, CS 708, cyanofenphos, cyanophos, cyclethrin, cythioate, d-tetramethrin, DAEP, dazomet, decarbofuran, diamidafos, dicapthon, dichlofenthion, dicresyl, dicyclanil, dieldrin, diethyl 5-methylpyrazol-3-yl phosphate, dilor, dimefluthrin, dimetan, dimethrin, dimethylvinphos, dimetilan, dinoprop, dinosam, dinoseb, diofenolan, dioxabenzofos, dithicrofos, DSP, ecdysterone, El 1642, EMPC, EPBP, etaphos, ethiofencarb, ethyl formate, ethylene dibromide, ethylene dichloride, ethylene oxide, EXD, fenchlorphos, fenethacarb, fenitrothion, fenoxacrim, fenpirithrin, fensulfothion, fenthion-ethyl, flucofuron, fosmethilan, fospirate, fosthietan, furathiocarb, furethrin, guazatine, guazatine acetates, sodium tetrathiocarbonate, halfenprox, HCH, HEOD, heptachlor, heterophos, HHDN, hydrogen cyanide, hyquincarb, IPSP, isazofos, isobenzan, isodrin, isofenphos, isolane, isoprothiolane, isoxathion, juvenile hormone I,juvenile hormone II, juvenile hormone Ill, kelevan, kinoprene, lead arsenate, leptophos, lirimfos, lythidathion, m-cumenyl methylcarbamate, magnesium phosphide, mazidox, mecarphon, menazon, mercurous chloride, mesulfenfos, metam, metam-potassium, metam-sodium, methanesulfonyl fluoride, methocrotophos, methoprene, methothrin, methoxychlor, methyl isothiocyanate, methylchloroform, methylene chloride, metoxadiazone, mirex, naftalofos, naphthalene, NC-170, nicotine, nicotine sulfate, nithiazine, nornicotine, O-5-dichloro-4-iodophenyl O-ethyl ethylphosphonothioate, 0,0-diethyl O-4-methyl-2-oxo-2H-chromen-7-yl phosphorothioate, O,O-diethyl O-6-methyl-2-propylpyrimidin-4-yl phosphorothioate, O,O,O',O'-tetrapropyl dithiopyrophosphate, oleic acid, para-dichlorobenzene, parathion-methyl, pentachlorophenol, pentachlorophenyl laurate, PH 60-38, phenkapton, phosnichlor, phosphine, phoxim-methyl, pirimetaphos, polychlorodicyclopentadiene isomers, potassium arsenite, potassium thiocyanate, precocene I, precocene II, precocene Ill, primidophos, profluthrin, promecarb, prothiofos, pyrazophos, pyresmethrin, quassia, quinalphos-methyl, quinothion, rafoxanide, resmethrin, rotenone, kadethrin, ryania, ryanodine, sabadilla), schradan, sebufos, SI-0009, thiapronil, sodium arsenite, sodium cyanide, sodium fluoride, sodium hexafluorosilicate, sodium pentachlorophenoxide, sodium selenate, sodium thiocyanate, sulcofuron, sulcofuron-sodium, sulfuryl fluoride, sulprofos, tar oils, tazimcarb, TDE, tebupirimfos, temephos, terallethrin, tetrachloroethane, thicrofos, thiocyclam, thiocyclam hydrogen oxalate, thionazin, thiosultap, thiosultap-sodium, tralomethrin, transpermethrin, triazamate, trichlormetaphos-3, trichloronat, trimethacarb, tolprocarb, triclopyricarb, triprene, veratridine, veratrine, XMC, zetamethrin, zinc phosphide, zolaprofos, and meperfluthrin, tetramethylfluthrin, bis (tributyltin) oxide, bromoacetamide, ferric phosphate, niclosamide-olamine, tributyltin oxide, pyrimorph, trifenmorph, 1,2-dibromo-3-chloropropane, 1,3-dichloropropene, 3,4-dichlorotetrahydrothiophene 1,1-dioxide, 3-(4-chlorophenyl)-5-methylrhodanine, 5-methyl-6-thioxo-1,3,5-thiadiazinan-3-ylacetic acid, 6-isopentenylaminopurine, anisiflupurin, benclothiaz, cytokinins, DCIP, furfural, isamidofos, kinetin, *Myrothecium* verrucaria composition, tetrachlorothiophene, xylenols, zeatin, potassium ethylxanthate, acibenzolar, acibenzolar-S-methyl, *Reynoutria sachalinensis* extract, alpha-chlorohydrin, antu, barium carbonate, bisthiosemi, brodifacoum, bromadiolone, bromethalin, chlorophacinone, cholecalciferol, coumachlor, coumafuryl, coumatetralyl, crimidine, difenacoum, difethialone, diphacinone, ergocalciferol, flocoumafen, fluoroacetamide, flupropadine, flupropadine hydrochloride, norbormide, phosacetim, phosphorus, pindone, pyrinuron, scilliroside, sodium fluoroacetate, thallium sulfate, warfarin, 2-(2-butoxyethoxy)ethyl piperonylate, 5-(1,3-benzodioxol-5-yl)-3-hexylcyclohex-2-enone, farnesol with nerolidol, verbutin, MGK 264, piperonyl butoxide, piprotal, propyl isomer, S421, sesamex, sesasmolin, sulfoxide, anthraquinone, copper naphthenate, copper oxychloride, dicyclopentadiene, thiram, zinc naphthenate, ziram, imanin, ribavirin, chloroinconazide, mercuric oxide, thiophanate-methyl, azaconazole, bitertanol, bromuconazole, cyproconazole, difenoconazole, diniconazole, epoxiconazole, fenbuconazole, fluquinconazole, flusilazole, flutriafol, furametpyr, hexaconazole, imazalil, imibencon-azole, ipconazole, metconazole, myclobutanil, paclobutrazole, pefurazoate, penconazole, prothioconazole, pyrifenox, prochloraz, propiconazole, pyrisoxazole, simeconazole, tebuconazole, tetraconazole, triadimefon, triadimenol, triflumizole, triticonazole, ancymidol, fenarimol, nuarimol, bupirimate, dimethirimol, ethirimol, dodemorph, fenpropidin, fenpropimorph, spiroxamine, tridemorph, cyprodinil, mepanipyrim, pyrimethanil, fenpiclonil, fludioxonil, benalaxyl, furalaxyl, metalaxyl, R-metalaxyl, ofurace, oxadixyl, carbendazim, debacarb, fuberidazole, thiabendazole, chlozolinate, dichlozoline, myclozoline, procymidone, vinclozoline, boscalid, carboxin, fenfuram, flutolanil, mepronil, oxycarboxin, penthiopyrad, thifluzamide, dodine, iminoctadine, azoxystrobin, dimoxystrobin, enestroburin, fenaminstrobin, flufenoxystrobin, fluoxastrobin, kresoxim-methyl, metominostrobin, trifloxystrobin, orysastrobin, picoxystrobin, pyraclostrobin, pyrametostrobin, pyraoxystrobin, ferbam, mancozeb, maneb, metiram, propineb, zineb, captafol, captan, fluoroimide, folpet, tolylfluanid, bordeaux mixture, copper oxide, mancopper, oxine-copper, nitrothal-isopropyl, edifenphos, iprobenphos, phosdiphen, tolclofos-methyl, anilazine, benthiavalicarb, blasticidin-S, chloroneb, chlorothalonil, cyflufenamid, cymoxanil, cyclobutrifluram, diclocymet, diclomezine, dicloran, diethofencarb, dimetho-morph, flumorph, dithianon, ethaboxam, etridiazole, famoxadone, fenamidone, fenoxanil, ferimzone, fluazinam, flumetylsulforim, fluopicolide, fluoxytioconazole, flusulfamide, fluxapyroxad, fenhexamid, fosetyl-aluminium, hymexazol, iprovalicarb, cyazofamid, methasulfocarb, metrafenone, pencycuron, phthalide, polyoxins, propamocarb, pyribencarb, proquinazid, pyroquilon, pyriofenone, quinoxyfen, quintozene, tiadinil, triazoxide, tricyclazole, triforine, validamycin, valifenalate, zoxamide, mandipropamid, flubeneteram, isopyrazam, sedaxane, benzovindiflupyr, pydiflumetofen, 3-difluoromethyl-1-methyl-1H-pyrazole-4-carboxylic acid (3',4',5'-trifluoro-biphenyl-2-yl)-amide, isoflucypram, isotianil, dipymetitrone, 6-ethyl-5,7-dioxo-pyrrolo[4,5][1,4]dithiino[1,2-c]isothiazole-3-carbonitrile, 2-(difluoromethyl)-N-[3-ethyl-1,1-dimethyl-indan-4-yl] pyridine-3-carboxamide, 4-(2,6-difluorophenyl)-6-methyl-5-phenyl-pyridazine-3-carbonitrile, (R)-3-(difluoromethyl)-1-methyl-N-[1,1,3-trimethylindan-4-yl]pyrazole-4-carboxamide, 4-(2-bromo-4-fluoro-phenyl)-N-(2-chloro-6-fluoro-phenyl)-2,5-dimethyl-pyrazol-3-amine, 4-(2-bromo-4-fluorophenyl)-N-(2-chloro-6-fluorophenyl)-1, 3-dimethyl-1H-pyrazol-5-amine, fluindapyr, coumethoxystrobin (jiaxiangjunzhi), Ivbenmixianan, dichlobentiazox, mandestrobin, 3-(4,4-difluoro-3,4-dihydro-3,3-dimethylisoquinolin-1-yl)quinolone, 2-[2-fluoro-6-[(8-fluoro-2-methyl-3-quinolyl)oxy]phenyl]propan-2-ol, oxathiapiprolin, tert-butyl N-[6-[[[(1-methyltetrazol-5-yl)-phenyl-methylene] amino]oxymethyl]-2-pyridyl]carbamate, pyraziflumid, inpyrfluxam, trolprocarb, mefentrifluconazole, ipfentrifluconazole, 2-(difluoromethyl)-N-[(3R)-3-ethyl-1,1-dimethyl-indan-4-yl]pyridine-3-carboxamide, N'-(2,5-dimethyl-4-phenoxy-phenyl)-N-ethyl-N-methyl-formamidine, N'-[4-(4,5-dichlorothiazol-2-yl)oxy-2,5-dimethyl-phenyl]-N-ethyl-N-methyl-formamidine, [2-[3-[2-[1-[2-[3,5-bis (difluoromethyl)pyrazol-1-yl]acetyl]-4-piperidyl]thiazol-4-yl]-4,5-dihydroisoxazol-5-yl]-3-chloro-phenyl] methanesulfonate, but-3-ynyl N-[6-[[(Z)-[(1-methyltetrazol-5-yl)-phenyl-methylene]amino]oxymethyl]-2-pyridyl] carbamate, methyl N-[[5-[4-(2,4-dimethylphenyl)triazol-2-yl]-2-methyl-phenyl]methyl]carbamate, 3-chloro-6-methyl-5-phenyl-4-(2,4,6-trifluorophenyl)pyridazine, pyridachlometyl, 3-(difluoromethyl)-1-methyl-N-[1,1,3-trimethylindan-4-yl]pyrazole-4-carboxamide, 1-[2-[[1-(4-chlorophenyl)pyrazol-3-yl]oxymethyl]-3-methyl-phenyl]-4-methyl-tetrazol-5-one, 1-methyl-4-[3-methyl-2-[[2-methyl-4-(3,4,5-trimethylpyrazol-1-yl)phenoxy]methyl]phenyl] tetrazol-5-one, aminopyrifen, ametoctradin, amisulbrom, penflufen, (Z,2E)-5-[1-(4-chlorophenyl)pyrazol-3-yl]oxy-2-methoxyimino-N,3-dimethyl-pent-3-enamide, florylpicoxamid, fenpicoxamid, metarylpicoxamid, tebufloquin, ipflufenoquin, quinofumelin, is ofetamid, N-[2-[2,4-dichloro-phenoxy]phenyl]-3-(difluoromethyl)-1-methyl-pyrazole-4-carboxamide, N-[2-[2-chloro-4-(trifluoromethyl) phenoxy]phenyl]-3-(difluoromethyl)-1-methyl-pyrazole-4-carboxamide, benzothiostrobin, phenamacril, 5-amino-1,3,4-thiadiazole-2-thiol zinc salt (2:1), fluopyram, flufenoxadiazam, flutianil, fluopimomide, pyrapropoyne, picarbutrazox, 2-(difluoromethyl)-N-(3-ethyl-1,1-dimethyl-indan-4-yl)pyridine-3-carboxamide, 2-(difluoromethyl)-N-((3R)-1, 1, 3-trimethylindan-4-yl) pyridine-3-carboxamide, 4-[[6-[2-(2,4-difluorophenyl)-11-difluoro-2-hydroxy-3-(1, 2,4-triazol-1-yl)propyl]-3-pyridyl]oxy]benzonitrile, metyltetraprole, 2-(difluoromethyl)-N-((3R)-1, 1, 3-trimethylindan-4-yl) pyridine-3-carboxamide, α-(1, 1-dimethylethyl)-α-[4'-(trifluoromethoxy) [1, 1'-biphenyl]-4-yl]-5-pyrimidinemethanol, fluoxapiprolin, enoxastrobin, 4-[[6-[2-(2, 4-difluorophenyl)-1,1-difluoro-2-hydroxy-3-(1,2,4-triazol-1-yl)propyl]-3-pyridyl]oxy] benzonitrile, 4-[[6-[2-(2,4-difluorophenyl)-1,1-difluoro-2-hydroxy-3-(5-sulfanyl-1,2, 4-triazol-1-yl)propyl]-3-pyridyl]oxy]benzonitrile, 4-[[6-[2-(2,4-difluorophenyl)-1,1-difluoro-2-hydroxy-3-(5-thioxo-4H-1,2,4-triazol-1-yl)propyl]-3 pyridyl]oxy]benzonitrile, trinexapac, coumoxystrobin, zhongshengmycin, thiodiazole copper, zinc thiazole, amectotractin, iprodione, seboctylamine, N'-[5-bromo-2-methyl-6-[(1S)-1-methyl-2-propoxy-ethoxy]-3-pyridyl]-N-ethyl-N-methyl-formamidine, N'-[5-bromo-2-methyl-6-[(1R)-1-methyl-2-propoxy-ethoxy]-3-pyridyl]-N-ethyl-N-methyl-formamidine, N'-[5-bromo-2-methyl-6-(1-methyl-2-propoxy-ethoxy)-3-pyridyl]-N-ethyl-N-methyl-formamidine, N'-[5-chloro-2-methyl-6-(1-methyl-2-propoxy-ethoxy)-3-pyridyl]-N-ethyl-N-methyl-formamidine, N'-[5-bromo-2-methyl-6-(1-methyl-2-propoxy-ethoxy)-3-pyridyl]-N-isopropyl-N-methyl-formamidine (these compounds may be prepared from the methods described in WO2015/155075); N'-[5-bromo-2-methyl-6-(2-propoxypropoxy)-3-pyridyl]-N-ethyl-N- methyl-formamidine (this compound may be prepared from the methods described in IPCOM000249876D); N-isopropyl-N'-[5-methoxy-2-methyl-4-(2,2,2-trifluoro-1-hydroxy-1-phenyl-ethyl)phenyl]-N-methyl-formamidine, N'-[4-(1-cyclopropyl-2,2,2-trifluoro-1-hydroxy-ethyl)-5-methoxy-2-methyl-phenyl]-N-isopropyl-N-methyl-formamidine (these compounds may be prepared from the methods described in WO2018/228896); N-ethyl-N'-[5-methoxy-2-methyl-4-[(2-trifluoromethyl)oxetan-2-yl]phenyl]-N-methyl-formamidine, N-ethyl-N'-[5-methoxy-2-methyl-4-[(2-trifuoromethyl)tetrahydrofuran-2-yl]phenyl]-N-methyl-formamidine (these compounds may be prepared from the methods described in WO2019/110427); N-[(1R)-1-benzyl-3-chloro-1-methyl-but-3-enyl]-8-fluoro-quinoline-3-carboxamide, N-[(1S)-1-benzyl-3-chloro-1-methyl-but-3-enyl]-8-fluoro-quinoline-3-carboxamide, N-[(1R)-1-benzyl-3,3,3-trifluoro-1-methyl-propyl]-8-fluoro-quinoline-3-carboxamide, N-[(1S)-1-benzyl-3,3,3-trifluoro-1-methyl-propyl]-8-fluoro-quinoline-3-carboxamide, N-[(1R)-1-benzyl-1,3-dimethyl-butyl]-7,8-difluoro-quinoline-3-carboxamide, N-[(1S)-1-benzyl-1,3-dimethyl-butyl]-7,8-difluoro-quinoline-3-carboxamide, 8-fluoro-N-[(1R)-1-[(3-fluorophenyl)methyl]-1,3-dimethyl-butyl]quinoline-3-carboxamide, 8-fluoro-N-[(1S)-1-[(3-fluorophenyl)methyl]-1,3-dimethyl-butyl]quinoline-3-carboxamide, N-[(1R)-1-benzyl-1,3-dimethyl-butyl]-8-fluoro-quinoline-3-carboxamide, N-[(1S)-1-benzyl-1,3-dimethyl-butyl]-8-fluoro-quinoline-3-carboxamide, N-((1R)-1-benzyl-3-chloro-1-methyl-but-3-enyl)-8-fluoro-quinoline-3-carboxamide, N-((1S)-1-benzyl-3-chloro-1-methyl-but-3-enyl)-8-fluoro-quinoline-3-carboxamide (these compounds may be prepared from the methods described in WO2017/153380); 1-(6,7-dimethylpyrazolo[1,5-a]pyridin-3-yl)-4,4,5-trifluoro-3,3-dimethyl-isoquinoline, 1-(6,7-dimethylpyrazolo[1,5-a]pyridin-3-yl)-4,4,6-trifluoro-3,3-dimethyl-isoquinoline, 4,4-difluoro-3,3-dimethyl-1-(6-methylpyrazolo[1,5-a]pyridin-3-yl)isoquinoline, 4,4-difluoro-3,3-dimethyl-1-(7-methylpyrazolo[1,5-a]pyridin-3-yl)isoquinoline, 1-(6-chloro-7-methyl-pyrazolo[1,5-a]pyridin-3-yl)-4,4-difluoro-3,3-dimethyl-isoquinoline (these compounds may be prepared from the methods described in WO2017/025510); 1-(4,5-dimethylbenzimidazol-1-yl)-4,4,5-trifluoro-3,3-dimethyl-isoquinoline, 1-(4,5-dimethylbenzimidazol-1-yl)-4,4-difluoro-3,3-dimethyl-isoquinoline, 6-chloro-4,4-difluoro-3,3-dimethyl-1-(4-methylbenzimidazol-1-yl)isoquinoline, 4,4-difluoro-1-(5-fluoro-4-methyl-benzimidazol-1-yl)-3,3-dimethyl-isoquinoline, 3-(4,4-difluoro-3,3-dimethyl-1-isoquinolyl)-7,8-dihydro-6H-cyclopenta[e]benzimidazole (these compounds may be prepared from the methods described in WO2016/156085); N-methoxy-N-[[4-[5-(trifluoromethyl)-1,2,4-oxadiazol-3-yl]phenyl]methyl]cyclopropanecarboxamide, N,2-dimethoxy-N-[[4-[5-(trifluoromethyl)-1,2,4-oxadiazol-3-yl]phenyl]methyl]propanamide, N-ethyl-2-methyl-N-[[4-[5-(trifluoromethyl)-1,2,4-oxadiazol-3-yl]phenyl]methyl]propanamide, 1-methoxy-3-methyl-1-[[4-[5-(trifluoromethyl)-1,2,4-oxadiazol-3-yl]phenyl]methyl]urea, 1,3-dimethoxy-1-[[4-[5-(trifluoromethyl)-1,2,4-oxadiazol-3-yl]phenyl]methyl]urea, 3-ethyl-1-methoxy-1-[[4-[5-(trifluoromethyl)-1,2,4-oxadiazol-3-yl]phenyl]methyl]urea, N-[[4-[5-(trifluoromethyl)-1,2,4-oxadiazol-3-yl]phenyl]methyl]propanamide, 4,4-dimethyl-2-[[4-[5-(trifluoromethyl)-1,2,4-oxadiazol-3-yl]phenyl]methyl]isoxazolidin-3-one, 5,5-dimethyl-2-[[4-[5-(trifluoromethyl)-1,2,4-oxadiazol-3-yl]phenyl]methyl]isoxazolidin-3-one, ethyl 1-[[4-[5-(trifluoromethyl)-1,2,4-oxadiazol-3-yl]phenyl]methyl]pyrazole-4-carboxylate, N,N-dimethyl-1-[[4-[5-(trifluoromethyl)-1,2,4-oxadiazol-3-yl]phenyl]methyl]-1,2,4-triazol-3-amine (these compounds may be prepared from the methods described in WO 2017/055473, WO 2017/055469, WO 2017/093348 and WO 2017/118689); 2-[6-(4-chlorophenoxy)-2-(trifluoromethyl)-3-pyridyl]-1-(1,2,4-triazol-1-yl)propan-2-ol (this compound may be prepared from the methods described in WO 2017/029179); 2-[6-(4-bromophenoxy)-2-(trifluoromethyl)-3-pyridyl]-1-(1,2,4-triazol-1-yl)propan-2-oI (this compound may be prepared from the methods described in WO 2017/029179); 3-[2-(1-chlorocyclopropyl)-3-(2-fluorophenyl)-2-hydroxy-propyl]imidazole-4-carbonitrile (this compound may be prepared from the methods described in WO 2016/156290); 3-[2-(1-chlorocyclopropyl)-3-(3-chloro-2-fluoro-phenyl)-2-hydroxy-propyl]imidazole-4-carbonitrile (this compound may be prepared from the methods described in WO 2016/156290); (4-phenoxyphenyl)methyl 2-amino-6-methyl-pyridine-3-carboxylate (this compound may be prepared from the methods described in WO 2014/006945); 2,6-Dimethyl-1H,5H-[1,4]dithiino[2,3-c:5,6-c']dipyrrole-1,3,5,7(2H,6H)-tetrone (this compound may be prepared from the methods described in WO 2011/138281) N-methyl-4-[5-(trifluoromethyl)-1,2,4-oxadiazol-3-yl]benzenecarbothioamide; N-methyl-4-[5-(trifluoromethyl)-1,2,4-oxadiazol-3-yl]benzamide; (Z,2E)-5-[1-(2,4-dichlorophenyl)pyrazol-3-yl]oxy-2-methoxyimino-N,3-dimethyl-pent-3-enamide (this compound may be prepared from the methods described in WO 2018/153707); N'-(2-chloro-5-methyl-4-phenoxy-phenyl)-N-ethyl-N-methyl-formamidine; N'-[2-chloro-4-(2-fluorophenoxy)-5-methyl-phenyl]-N-ethyl-N-methyl-formamidine (this compound may be prepared from the methods described in WO 2016/202742); 2-(difluoromethyl)-N-[(3S)-3-ethyl-1,1-dimethyl-indan-4-yl]pyridine-3-carboxamide (this compound may be prepared from the methods described in WO 2014/095675); (5-methyl-2-pyridyl)-[4-[5-(trifluoromethyl)-1,2,4-oxadiazol-3-yl]phenyl]methanone, (3-methylisoxazol-5-yl)-[4-[5-(trifluoromethyl)-1,2,4-oxadiazol-3-yl]phenyl]methanone (these compounds may be prepared from the methods described in WO 2017/220485); 2-oxo-N-propyl-2-[4-[5-(trifluoromethyl)-1,2,4-oxadiazol-3-yl]phenyl]acetamide (this compound may be prepared from the methods described in WO 2018/065414); ethyl 1-[[5-[5-(trifluoromethyl)-1,2,4-oxadiazol-3-yl]-2-thienyl]methyl]pyrazole-4-carboxylate (this compound may be prepared from the methods described in WO 2018/158365); 2,2-difluoro-N-methyl-2-[4-[5-(trifluoromethyl)-1,2,4-oxadiazol-3-yl]phenyl]acetamide, N-[(E)-methoxyiminomethyl]-4-[5-(trifluoromethyl)-1,2,4-oxadiazol-3-yl]benzamide, N—[(Z)-methoxyiminomethyl]-4-[5-(trifluoromethyl)-1,2,4-oxadiazol-3-yl]benzamide, N—[N-methoxy-C-methyl-carbonimidoyl]-4-[5-(trifluoromethyl)-1,2,4-oxadiazol-3-yl]benzamide (these compounds may be prepared from the methods described in WO 2018/202428).

The compounds of the invention may also be used in combination with anthelmintic agents. Such anthelmintic agents include, compounds selected from the macrocyclic lactone class of compounds such as ivermectin, avermectin, abamectin, emamectin, eprinomectin, doramectin, selamectin, moxidectin, nemadectin and milbemycin derivatives as described in EP-357460, EP-444964 and EP-594291. Additional anthelmintic agents include semisynthetic and biosynthetic avermectin/milbemycin derivatives such as those described in U.S. Pat. No. 5,015,630, WO-9415944 and WO-9522552. Additional anthelmintic agents include the benzimidazoles such as albendazole, cambendazole, fenbendazole, flubendazole, mebendazole, oxfendazole, oxibendazole, parbendazole, and other members of the class. Additional anthelmintic agents include imidazothiazoles and tetrahydropyrimidines such as tetramisole, levamisole, pyrantel pamoate, oxantel or morantel. Additional anthelmintic agents include flukicides, such as triclabendazole and clorsulon and the cestocides, such as praziquantel and epsiprantel.

The compounds of the invention may be used in combination with derivatives and analogues of the paraherquamide/marcfortine class of anthelmintic agents, as well as the antiparasitic oxazolines such as those disclosed in U.S. Pat. Nos. 5,478,855, 4,639,771 and DE-19520936.

The compounds of the invention may be used in combination with derivatives and analogues of the general class of dioxomorpholine antiparasitic agents as described in WO-9615121 and also with anthelmintic active cyclic depsipeptides such as those described in WO-9611945, WO-9319053, WO-9325543, EP-626375, EP-382173, WO-9419334, EP-382173, and EP-503538.

The compounds of the invention may be used in combination with other ectoparasiticides; for example, fipronil; pyrethroids; organophosphates; insect growth regulators such as lufenuron; ecdysone agonists such as tebufenozide and the like; neonicotinoids such as imidacloprid and the like.

The compounds of the invention may be used in combination with terpene alkaloids, for example those described in WO 95/19363 or WO 04/72086, particularly the compounds disclosed therein.

Other examples of such biologically active compounds that the compounds of the invention may be used in combination with include but are not restricted to the following: Organophosphates: acephate, azamethiphos, azinphos-ethyl, azinphos-methyl, bromophos, bromophos-ethyl, cadusafos, chlorethoxyphos, chlorpyrifos, chlorfenvinphos, chlormephos, demeton, demeton-S-methyl, demeton-S-methyl sulphone, dialifos, diazinon, dichlorvos, dicrotophos, dimethoate, disulfoton, ethion, ethoprophos, etrimfos, famphur, fenamiphos, fenitrothion, fensulfothion, fenthion, flupyrazofos, fonofos, formothion, fosthiazate, heptenophos, isazophos, isothioate, isoxathion, malathion, methacriphos, methamidophos, methidathion, methyl-parathion, mevinphos, monocrotophos, naled, omethoate, oxydemeton-methyl, paraoxon, parathion, parathion-methyl, phenthoate, phosalone, phosfolan, phosphocarb, phosmet, phosphamidon, phorate, phoxim, pirimiphos, pirimiphos-methyl, profenofos, propaphos, proetamphos, prothiofos, pyraclofos, pyridapenthion, quinalphos, sulprophos, temephos, terbufos, tebupirimfos, tetrachlorvinphos, thimeton, triazophos, trichlorfon, vamidothion.

Carbamates: alanycarb, aldicarb, 2-sec-butylphenyl methylcarbamate, benfuracarb, carbaryl, carbofuran, carbosulfan, cloethocarb, ethiofencarb, fenoxycarb, fenthiocarb, furathiocarb, HCN-801, isoprocarb, indoxacarb, methiocarb, methomyl, 5-methyl-m-cumenylbutyryl(methyl)carbamate, oxamyl, pirimicarb, propoxur, thiodicarb, thiofanox, triazamate, UC-51717.

Pyrethroids: acrinathin, allethrin, alphametrin, 5-benzyl-3-furylmethyl (E)-(1R)-cis-2,2-dimethyl-3-(2-oxothiolan-3-ylidenemethyl)cyclopropanecarboxylate, bifenthrin, beta-cyfluthrin, cyfluthrin, a-cypermethrin, beta-cypermethrin, bioallethrin, bioallethrin((S)-cyclopentylisomer), bioresmethrin, bifenthrin, NCI-85193, cycloprothrin, cyhalothrin, cythithrin, cyphenothrin, deltamethrin, empenthrin, esfenvalerate, ethofenprox, fenfluthrin, fenpropathrin, fenvalerate, flucythrinate, flumethrin, fluvalinate (D isomer), imiprothrin, cyhalothrin, lambda-cyhalothrin, permethrin, phenothrin, prallethrin, pyrethrins (natural products), resmethrin, tetramethrin, transfluthrin, theta-cypermethrin, silafluofen, t-fluvalinate, tefluthrin, tralomethrin, Zeta-cypermethrin.

Arthropod growth regulators: a) chitin synthesis inhibitors: benzoylureas: chlorfluazuron, diflubenzuron, fluazuron, flucycloxuron, flufenoxuron, hexaflumuron, lufenuron, novaluron, teflubenzuron, triflumuron, buprofezin, diofenolan, hexythiazox, etoxazole, chlorfentazine; b) ecdysone antagonists: halofenozide, methoxyfenozide, tebufenozide; c) juvenoids: pyriproxyfen, methoprene (including S-methoprene), fenoxycarb; d) lipid biosynthesis inhibitors: spirodiclofen.

Other antiparasitics: acequinocyl, amitraz, AKD-1022, ANS-118, azadirachtin, *Bacillus thuringiensis*, bensultap, bifenazate, binapacryl, bromopropylate, BTG-504, BTG-505, camphechlor, cartap, chlorobenzilate, chlordimeform, chlorfenapyr, chromafenozide, clothianidine, cyromazine, diacloden, diafenthiuron, DBI-3204, dinactin, dihydroxymethyldihydroxypyrrolidine, dinobuton, dinocap, endosulfan, ethiprole, ethofenprox, fenazaquin, flumite, MTI-800, fenpyroximate, fluacrypyrim, flubenzimine, flubrocythrinate, flufenzine, flufenprox, fluproxyfen, halofenprox, hydramethylnon, IKI-220, kanemite, NC-196, neem guard, nidinorterfuran, nitenpyram, SD-35651, WL-108477, pirydaryl, propargite, protrifenbute, pymethrozine, pyridaben, pyrimidifen, NC-1111, R-195, RH-0345, RH-2485, RYI-210, S-1283, S-1833, SI-8601, silafluofen, silomadine, spinosad, tebufenpyrad, tetradifon, tetranactin, thiacloprid, thiocyclam, thiamethoxam, tolfenpyrad, triazamate, triethoxyspinosyn, trinactin, verbutin, vertalec, YI-5301.

Biological agents: *Bacillus thuringiensis* ssp *aizawai*, kurstaki, *Bacillus thuringiensis* delta endotoxin, baculovirus, entomopathogenic bacteria, virus and fungi.

Bactericides: chlortetracycline, oxytetracycline, streptomycin. Other biological agents: enrofloxacin, febantel, penethamate, moloxicam, cefalexin, kanamycin, pimobendan, clenbuterol, omeprazole, tiamulin, benazepril, pyriprole, cefquinome, florfenicol, buserelin, cefovecin, tulathromycin, ceftiour, carprofen, metaflumizone, praziquarantel, triclabendazole.

Another aspect of invention is related to the use of a compound of formula (I) or of a preferred individual compound as above-defined, of a composition comprising at least one compound of formula (I) or at least one preferred individual compound as above-defined, or of a fungicidal or insecticidal mixture comprising at least one compound of formula (I) or at least one preferred individual compound as above-defined, in admixture with other fungicides or insecticides as described above, for controlling or preventing infestation of plants, e.g. useful plants such as crop plants, propagation material thereof, e.g. seeds, harvested crops, e.g., harvested food crops, or non-living materials by insects or by phytopathogenic microorganisms, preferably fungal organisms.

A further aspect of invention is related to a method of controlling or preventing an infestation of plants, e.g., useful plants such as crop plants, propagation material thereof, e.g. seeds, harvested crops, e.g. harvested food crops, or of non-living materials by insects or by phytopathogenic or spoilage microorganisms or organisms potentially harmful to man, especially fungal organisms, which comprises the application of a compound of formula (I) or of a preferred individual compound as above-defined as active ingredient to the plants, to parts of the plants or to the locus thereof, to the propagation material thereof, or to any part of the non-living materials.

Controlling or preventing means reducing infestation by insects or by phytopathogenic or spoilage microorganisms or organisms potentially harmful to man, especially fungal organisms, to such a level that an improvement is demonstrated.

A preferred method of controlling or preventing an infestation of crop plants by phytopathogenic microorganisms, especially fungal organisms, or insects which comprises the application of a compound of formula (I), or an agrochemical composition which contains at least one of said compounds, is foliar application. The frequency of application and the rate of application will depend on the risk of infestation by the corresponding pathogen or insect. However, the compounds of formula (I) can also penetrate the plant through the roots via the soil (systemic action) by drenching the locus of the plant with a liquid formulation, or by applying the compounds in solid form to the soil, e.g., in granular form (soil application). In crops of water rice such granulates can be applied to the flooded rice field. The compounds of formula (I) may also be applied to seeds (coating) by impregnating the seeds or tubers either with a liquid formulation of the fungicide or coating them with a solid formulation.

A formulation, e.g. a composition containing the compound of formula (I), and, if desired, a solid or liquid adjuvant or monomers for encapsulating the compound of formula (I), may be prepared in a known manner, typically by intimately mixing and/or grinding the compound with extenders, for example solvents, solid carriers and, optionally, surface active compounds (surfactants).

Advantageous rates of application are normally from 5 g to 2 kg of active ingredient (a.i.) per hectare (ha), preferably from 10 g to 1 kg a.i./ha, most preferably from 20 g to 600 g a.i./ha. When used as seed drenching agent, convenient dosages are from 10 mg to 1 g of active substance per kg of seeds.

When the combinations of the present invention are used for treating seed, rates of 0.001 to 50 g of a compound of formula (I) per kg of seed, preferably from 0.01 to 10 g per kg of seed are generally sufficient.

The compositions of the invention may be employed in any conventional form, for example in the form of a twin pack, a powder for dry seed treatment (DS), an emulsion for seed treatment (ES), a flowable concentrate for seed treatment (FS), a solution for seed treatment (LS), a water dispersible powder for seed treatment (WS), a capsule suspension for seed treatment (CF), a gel for seed treatment (GF), an emulsion concentrate (EC), a suspension concentrate (SC), a suspo-emulsion (SE), a capsule suspension (CS), a water dispersible granule (WG), an emulsifiable granule (EG), an emulsion, water in oil (EO), an emulsion, oil in water (EW), a micro-emulsion (ME), an oil dispersion (OD), an oil miscible flowable (OF), an oil miscible liquid (OL), a soluble concentrate (SL), an ultra-low volume suspension (SU), an ultra-low volume liquid (UL), a technical concentrate (TK), a dispersible concentrate (DC), a wettable powder (WP) or any technically feasible formulation in combination with agriculturally acceptable adjuvants.

Such compositions may be produced in conventional manner, e.g., by mixing the active ingredients with appropriate formulation inerts (diluents, solvents, fillers and optionally other formulating ingredients such as surfactants, biocides, anti-freeze, stickers, thickeners and compounds that provide adjuvancy effects). Also conventional slow release formulations may be employed where long lasting efficacy is intended. Particularly formulations to be applied in spraying forms, such as water dispersible concentrates (e.g. EC, SC, DC, OD, SE, EW, EO and the like), wettable powders and granules, may contain surfactants such as wetting and dispersing agents and other compounds that provide adjuvancy effects, e.g. the condensation product of formaldehyde with naphthalene sulphonate, an alkylarylsulphonate, a lignin sulphonate, a fatty alkyl sulphate, and ethoxylated alkylphenol and an ethoxylated fatty alcohol.

A seed dressing formulation is applied in a manner known per se to the seeds employing the combination of the invention and a diluent in suitable seed dressing formulation form, e.g., as an aqueous suspension or in a dry powder form having good adherence to the seeds. Such seed dressing formulations are known in the art. Seed dressing formulations may contain the single active ingredients or the combination of active ingredients in encapsulated form, e.g. as slow release capsules or microcapsules.

In general, the formulations include from 0.01 to 90% by weight of active agent, from 0 to 20% agriculturally acceptable surfactant and 10 to 99.99% solid or liquid formulation inerts and adjuvant(s), the active agent consisting of at least the compound of formula (I) together with component (B) and (C), and optionally other active agents, particularly microbiocides or conservatives or the like. Concentrated forms of compositions generally contain in between about 2 and 80%, preferably between about 5 and 70% by weight of active agent. Application forms of formulation may for example contain from 0.01 to 20% by weight, preferably from 0.01 to 5% by weight of active agent. Whereas commercial products will preferably be formulated as concentrates, the end user will normally employ diluted formulations.

Table 1 below illustrates examples of individual compounds of formula (I) according to the invention.

Table A-1 provides 48 compounds A-1.001 to A-1.048 of formula (Ib)

(Ib)

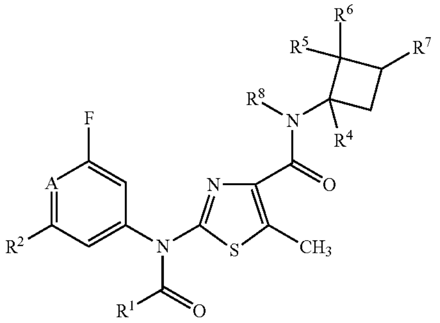

wherein A is N, $R^7$ is hydrogen, $R^1$ is tetrahydrofuran-3-yl, $R^2$ is hydrogen, and $R^4$, $R^5$, $R^6$ and $R^8$ are as defined in Table 1.

TABLE 1

Individual compounds of formula (I) according to the invention

| Cpd No. | $R^4$ | $R^5$ | $R^6$ | $R^8$ |
|---|---|---|---|---|
| 001 | hydrogen | hydrogen | hydrogen | hydrogen |
| 002 | hydrogen | methyl | hydrogen | hydrogen |
| 003 | hydrogen | hydrogen | methyl | hydrogen |
| 004 | hydrogen | methyl | methyl | hydrogen |
| 005 | methyl | hydrogen | hydrogen | hydrogen |
| 006 | methyl | methyl | hydrogen | hydrogen |

TABLE 1-continued

| Individual compounds of formula (I) according to the invention | | | | |
|---|---|---|---|---|
| Cpd No. | $R^4$ | $R^5$ | $R^6$ | $R^8$ |
| 007 | methyl | hydrogen | methyl | hydrogen |
| 008 | methyl | methyl | methyl | hydrogen |
| 009 | ethyl | hydrogen | hydrogen | hydrogen |
| 010 | ethyl | methyl | hydrogen | hydrogen |
| 011 | ethyl | hydrogen | methyl | hydrogen |
| 012 | ethyl | methyl | methyl | hydrogen |
| 013 | hydrogen | hydrogen | hydrogen | tetrahydrofuran-3-carbonyl |
| 014 | hydrogen | methyl | hydrogen | tetrahydrofuran-3-carbonyl |
| 015 | hydrogen | hydrogen | methyl | tetrahydrofuran-3-carbonyl |
| 016 | hydrogen | methyl | methyl | tetrahydrofuran-3-carbonyl |
| 017 | methyl | hydrogen | hydrogen | tetrahydrofuran-3-carbonyl |
| 018 | methyl | methyl | hydrogen | tetrahydrofuran-3-carbonyl |
| 019 | methyl | hydrogen | methyl | tetrahydrofuran-3-carbonyl |
| 020 | methyl | methyl | methyl | tetrahydrofuran-3-carbonyl |
| 021 | ethyl | hydrogen | hydrogen | tetrahydrofuran-3-carbonyl |
| 022 | ethyl | methyl | hydrogen | tetrahydrofuran-3-carbonyl |
| 023 | ethyl | hydrogen | methyl | tetrahydrofuran-3-carbonyl |
| 024 | ethyl | methyl | methyl | tetrahydrofuran-3-carbonyl |
| 025 | hydrogen | hydrogen | hydrogen | tetrahydrofuran-2-carbonyl |
| 026 | hydrogen | methyl | hydrogen | tetrahydrofuran-2-carbonyl |
| 027 | hydrogen | hydrogen | methyl | tetrahydrofuran-2-carbonyl |
| 028 | hydrogen | methyl | methyl | tetrahydrofuran-2-carbonyl |
| 029 | methyl | hydrogen | hydrogen | tetrahydrofuran-2-carbonyl |
| 030 | methyl | methyl | hydrogen | tetrahydrofuran-2-carbonyl |
| 031 | methyl | hydrogen | methyl | tetrahydrofuran-2-carbonyl |
| 032 | methyl | methyl | methyl | tetrahydrofuran-2-carbonyl |
| 033 | ethyl | hydrogen | hydrogen | tetrahydrofuran-2-carbonyl |
| 034 | ethyl | methyl | hydrogen | tetrahydrofuran-2-carbonyl |
| 035 | ethyl | hydrogen | methyl | tetrahydrofuran-2-carbonyl |
| 036 | ethyl | methyl | methyl | tetrahydrofuran-2-carbonyl |
| 037 | hydrogen | hydrogen | hydrogen | oxetane-3-carbonyl |
| 038 | hydrogen | methyl | hydrogen | oxetane-3-carbonyl |
| 039 | hydrogen | hydrogen | methyl | oxetane-3-carbonyl |
| 040 | hydrogen | methyl | methyl | oxetane-3-carbonyl |
| 041 | methyl | hydrogen | hydrogen | oxetane-3-carbonyl |
| 042 | methyl | methyl | hydrogen | oxetane-3-carbonyl |
| 043 | methyl | hydrogen | methyl | oxetane-3-carbonyl |
| 044 | methyl | methyl | methyl | oxetane-3-carbonyl |
| 045 | ethyl | hydrogen | hydrogen | oxetane-3-carbonyl |
| 046 | ethyl | methyl | hydrogen | oxetane-3-carbonyl |
| 047 | ethyl | hydrogen | methyl | oxetane-3-carbonyl |
| 048 | ethyl | methyl | methyl | oxetane-3-carbonyl |

Table A-2 provides 48 compounds A-2.001 to A-2.048 of Formula (Ib), wherein A is N, $R^7$ is hydrogen, $R^1$ is tetrahydrofuran-3-yl, $R^2$ is fluoro, and $R^4$, $R^5$, $R^6$ and $R^8$ are as defined in Table 1.

Table A-3 provides 48 compounds A-3.001 to A-3.048 of Formula (Ib), wherein A is N, $R^7$ is hydrogen, $R^1$ is tetrahydrofuran-2-yl, $R^2$ is hydrogen, and $R^4$, $R^5$, $R^6$ and $R^8$ are as defined in Table 1.

Table A-4 provides 48 compounds A-4.001 to A-4.048 of Formula (Ib), wherein A is N, $R^7$ is hydrogen, $R^1$ is tetrahydrofuran-2-yl, $R^2$ is fluoro, and $R^4$, $R^5$, $R^6$ and $R^8$ are as defined in Table 1.

Table A-5 provides 48 compounds A-5.001 to A-5.048 of Formula (Ib), wherein A is N, $R^7$ is hydrogen, $R^1$ is oxetane-3-yl, $R^2$ is hydrogen, and $R^4$, $R^5$, $R^6$ and $R^8$ are as defined in Table 1.

Table A-6 provides 48 compounds A-6.001 to A-6.048 of Formula (Ib), wherein A is N, $R^7$ is hydrogen, $R^1$ is oxetane-3-yl, $R^2$ is fluoro, and $R^4$, $R^5$, $R^6$ and $R^3$ are as defined in Table 1.

Table A-7 provides 48 compounds A-7.001 to A-7.048 of Formula (Ib), wherein A is N, $R^7$ is hydrogen, $R^1$ is 1-methylsulfonylethyl, $R^2$ is hydrogen, and $R^4$, $R^5$, $R^6$ and $R^8$ are as defined in Table 1.

Table A-8 provides 48 compounds A-8.001 to A-8.048 of Formula (Ib), wherein A is N, $R^7$ is hydrogen, $R^1$ is 1-methylsulfonylethyl, $R^2$ is fluoro, and $R^4$, $R^5$, $R^6$ and $R^8$ are as defined in Table 1.

Table A-9 provides 48 compounds A-9.001 to A-9.048 of Formula (Ib), wherein A is N, $R^7$ is hydrogen, $R^1$ is 1-methylsulfinylethyl, $R^2$ is hydrogen, and $R^4$, $R^5$, $R^6$ and $R^8$ are as defined in Table 1.

Table A-10 provides 48 compounds A-10.001 to A-10.048 of Formula (Ib), wherein A is N, $R^7$ is hydrogen, $R^1$ is 1-methylsulfinylethyl, $R^2$ is fluoro, and $R^4$, $R^5$, $R^6$ and $R^8$ are as defined in Table 1.

Table A-11 provides 48 compounds A-11.001 to A-11.048 of Formula (Ib), wherein A is N, $R^7$ is hydrogen, $R^1$ is 1-methylsulfanylethyl, $R^2$ is hydrogen, and $R^4$, $R^5$, $R^6$ and $R^8$ are as defined in Table 1.

Table A-12 provides 48 compounds A-12.001 to A-12.048 of Formula (Ib), wherein A is N, $R^7$ is hydrogen, $R^1$ is 1-methylsulfanylethyl, $R^2$ is fluoro, and $R^4$, $R^5$, $R^6$ and $R^8$ are as defined in Table 1.

Table A-13 provides 48 compounds A-13.001 to A-13.048 of Formula (Ib), wherein A is N, $R^7$ is hydrogen, $R^1$ is 1-methoxyethyl, $R^2$ is hydrogen, and $R^4$, $R^5$, $R^6$ and $R^8$ are as defined in Table 1.

Table A-14 provides 48 compounds A-14.001 to A-14.048 of Formula (Ib), wherein A is N, $R^7$ is hydrogen, $R^1$ is 1-methoxyethyl, $R^2$ is fluoro, and $R^4$, $R^5$, $R^6$ and $R^8$ are as defined in Table 1.

Table A-15 provides 48 compounds A-15.001 to A-15.048 of Formula (Ib), wherein A is N, $R^7$ is hydrogen, $R^1$ is 1-isopropoxyethyl, $R^2$ is hydrogen, and $R^4$, $R^5$, $R^6$ and $R^8$ are as defined in Table 1.

Table A-16 provides 48 compounds A-16.001 to A-16.048 of Formula (Ib), wherein A is N, $R^7$ is hydrogen, $R^1$ is 1-isopropoxyethyl, $R^2$ is fluoro, and $R^4$, $R^5$, $R^6$ and $R^8$ are as defined in Table 1.

Table A-17 provides 48 compounds A-17.001 to A-17.048 of Formula (Ib), wherein A is N, $R^7$ is hydrogen, $R^1$ is 1-tert-butoxyethyl, $R^2$ is hydrogen, and $R^4$, $R^5$, $R^6$ and $R^8$ are as defined in Table 1.

Table A-18 provides 48 compounds A-18.001 to A-18.048 of Formula (Ib), wherein A is N, $R^7$ is hydrogen, $R^1$ is 1-tert-butoxyethyl, $R^2$ is fluoro, and $R^4$, $R^5$, $R^6$ and $R^8$ are as defined in Table 1.

Table A-19 provides 48 compounds A-19.001 to A-19.048 of Formula (Ib), wherein A is N, $R^7$ is hydrogen, $R^1$ is isopropoxymethyl, $R^2$ is hydrogen, and $R^4$, $R^5$, $R^6$ and $R^8$ are as defined in Table 1.

Table A-20 provides 48 compounds A-20.001 to A-20.048 of Formula (Ib), wherein A is N, $R^7$ is hydrogen, $R^1$ is isopropoxymethyl, $R^2$ is fluoro, and $R^4$, $R^5$, $R^6$ and $R^8$ are as defined in Table 1.

Table A-21 provides 48 compounds A-21.001 to A-21.048 of Formula (Ib), wherein A is N, $R^7$ is hydrogen, $R^1$ is tert-butoxymethyl, $R^2$ is hydrogen, and $R^4$, $R^5$, $R^6$ and $R^8$ are as defined in Table 1.

Table A-22 provides 48 compounds A-22.001 to A-22.048 of Formula (Ib), wherein A is N, $R^7$ is hydrogen, $R^1$ is tert-butoxymethyl, $R^2$ is fluoro, and $R^4$, $R^5$, $R^6$ and $R^8$ are as defined in Table 1.

Table A-23 provides 48 compounds A-23.001 to A-23.048 of Formula (Ib), wherein A is N, $R^7$ is $—C(O)_2CH_3$, $R^1$ is tetrahydrofuran-3-yl, $R^2$ is hydrogen, and $R^4$, $R^5$, $R^6$ and $R^8$ are as defined in Table 1.

Table A-24 provides 48 compounds A-24.001 to A-24.048 of Formula (Ib), wherein A is N, $R^7$ is —$C(O)_2CH_3$, $R^1$ is tetrahydrofuran-3-yl, $R^2$ is fluoro, and $R^4$, $R^5$, $R^6$ and $R^8$ are as defined in Table 1.

Table A-25 provides 48 compounds A-25.001 to A-25.048 of Formula (Ib), wherein A is N, $R^7$ is —$C(O)_2CH_3$, $R^1$ is tetrahydrofuran-2-yl, $R^2$ is hydrogen, and $R^4$, $R^5$, $R^6$ and $R^8$ are as defined in Table 1.

Table A-26 provides 48 compounds A-26.001 to A-26.048 of Formula (Ib), wherein A is N, $R^7$ is —$C(O)_2CH_3$, $R^1$ is tetrahydrofuran-2-yl, $R^2$ is fluoro, and $R^4$, $R^5$, $R^6$ and $R^8$ are as defined in Table 1.

Table A-27 provides 48 compounds A-27.001 to A-27.048 of Formula (Ib), wherein A is N, $R^7$ is —$C(O)_2CH_3$, $R^1$ is oxetane-3-yl, $R^2$ is hydrogen, and $R^4$, $R^5$, $R^6$ and $R^8$ are as defined in Table 1.

Table A-28 provides 48 compounds A-28.001 to A-28.048 of Formula (Ib), wherein A is N, $R^7$ is —$C(O)_2CH_3$, $R^1$ is oxetane-3-yl, $R^2$ is fluoro, and $R^4$, $R^5$, $R^6$ and $R^8$ are as defined in Table 1.

Table A-29 provides 48 compounds A-29.001 to A-29.048 of Formula (Ib), wherein A is N, $R^7$ is —$C(O)_2CH_3$, $R^1$ is 1-methylsulfonylethyl, $R^2$ is hydrogen, and $R^4$, $R^5$, $R^6$ and $R^8$ are as defined in Table 1.

Table A-30 provides 48 compounds A-30.001 to A-30.048 of Formula (Ib), wherein A is N, $R^7$ is —$C(O)_2CH_3$, $R^1$ is 1-methylsulfonylethyl, $R^2$ is fluoro, and $R^4$, $R^5$, $R^6$ and $R^8$ are as defined in Table 1.

Table A-31 provides 48 compounds A-31.001 to A-31.048 of Formula (Ib), wherein A is N, $R^7$ is —$C(O)_2CH_3$, $R^1$ is 1-methylsulfinylethyl, $R^2$ is hydrogen, and $R^4$, $R^5$, $R^6$ and $R^8$ are as defined in Table 1.

Table A-32 provides 48 compounds A-32.001 to A-32.048 of Formula (Ib), wherein A is N, $R^7$ is —$C(O)_2CH_3$, $R^1$ is 1-methylsulfinylethyl, $R^2$ is fluoro, and $R^4$, $R^5$, $R^6$ and $R^8$ are as defined in Table 1.

Table A-33 provides 48 compounds A-33.001 to A-33.048 of Formula (Ib), wherein A is N, $R^7$ is —$C(O)_2CH_3$, $R^1$ is 1-methylsulfanylethyl, $R^2$ is hydrogen, and $R^4$, $R^5$, $R^6$ and $R^8$ are as defined in Table 1.

Table A-34 provides 48 compounds A-34.001 to A-34.048 of Formula (Ib), wherein A is N, $R^7$ is —$C(O)_2CH_3$, $R^1$ is 1-methylsulfanylethyl, $R^2$ is fluoro, and $R^4$, $R^5$, $R^6$ and $R^8$ are as defined in Table 1.

Table A-35 provides 48 compounds A-35.001 to A-35.048 of Formula (Ib), wherein A is N, $R^7$ is —$C(O)_2CH_3$, $R^1$ is 1-methoxyethyl, $R^2$ is hydrogen, and $R^4$, $R^5$, $R^6$ and $R^8$ are as defined in Table 1.

Table A-36 provides 48 compounds A-36.001 to A-36.048 of Formula (Ib), wherein A is N, $R^7$ is —$C(O)_2CH_3$, $R^1$ is 1-methoxyethyl, $R^2$ is fluoro, and $R^4$, $R^5$, $R^6$ and $R^8$ are as defined in Table 1.

Table A-37 provides 48 compounds A-37.001 to A-37.048 of Formula (Ib), wherein A is N, $R^7$ is —$C(O)_2CH_3$, $R^1$ is 1-isopropoxyethyl, $R^2$ is hydrogen, and $R^4$, $R^5$, $R^6$ and $R^8$ are as defined in Table 1.

Table A-38 provides 48 compounds A-38.001 to A-38.048 of Formula (Ib), wherein A is N, $R^7$ is —$C(O)_2CH_3$, $R^1$ is 1-isopropoxyethyl, $R^2$ is fluoro, and $R^4$, $R^5$, $R^6$ and $R^8$ are as defined in Table 1.

Table A-39 provides 48 compounds A-39.001 to A-39.048 of Formula (Ib), wherein A is N, $R^7$ is —$C(O)_2CH_3$, $R^1$ is 1-tert-butoxyethyl, $R^2$ is hydrogen, and $R^4$, $R^5$, $R^6$ and $R^8$ are as defined in Table 1.

Table A-40 provides 48 compounds A-40.001 to A-40.048 of Formula (Ib), wherein A is N, $R^7$ is —$C(O)_2CH_3$, $R^1$ is 1-tert-butoxyethyl, $R^2$ is fluoro, and $R^4$, $R^5$, $R^6$ and $R^8$ are as defined in Table 1.

Table A-41 provides 48 compounds A-41.001 to A-41.048 of Formula (Ib), wherein A is N, $R^7$ is —$C(O)_2CH_3$, $R^1$ is isopropoxymethyl, $R^2$ is hydrogen, and $R^4$, $R^5$, $R^6$ and $R^8$ are as defined in Table 1.

Table A-42 provides 48 compounds A-42.001 to A-42.048 of Formula (Ib), wherein A is N, $R^7$ is —$C(O)_2CH_3$, $R^1$ is isopropoxymethyl, $R^2$ is fluoro, and $R^4$, $R^5$, $R^6$ and $R^3$ are as defined in Table 1.

Table A-43 provides 48 compounds A-43.001 to A-43.048 of Formula (Ib), wherein A is N, $R^7$ is —$C(O)_2CH_3$, $R^1$ is tert-butoxymethyl, $R^2$ is hydrogen, and $R^4$, $R^5$, $R^6$ and $R^8$ are as defined in Table 1.

Table A-44 provides 48 compounds A-44.001 to A-44.048 of Formula (Ib), wherein A is N, $R^7$ is —$C(O)_2CH_3$, $R^1$ is tert-butoxymethyl, $R^2$ is fluoro, and $R^4$, $R^5$, $R^6$ and $R^8$ are as defined in Table 1.

Table A-45 provides 48 compounds A-45.001 to A-45.048 of Formula (Ib), wherein A is N, $R^7$ is —$C(O)_2CH_2CH_3$, $R^1$ is tetrahydrofuran-3-yl, $R^2$ is hydrogen, and $R^4$, $R^5$, $R^6$ and $R^8$ are as defined in Table 1.

Table A-46 provides 48 compounds A-46.001 to A-46.048 of Formula (Ib), wherein A is N, $R^7$ is —$C(O)_2CH_2CH_3$, $R^1$ is tetrahydrofuran-3-yl, $R^2$ is fluoro, and $R^4$, $R^5$, $R^6$ and $R^8$ are as defined in Table 1.

Table A-47 provides 48 compounds A-47.001 to A-47.048 of Formula (Ib), wherein A is N, $R^7$ is —$C(O)_2CH_2CH_3$, $R^1$ is tetrahydrofuran-2-yl, $R^2$ is hydrogen, and $R^4$, $R^5$, $R^6$ and $R^8$ are as defined in Table 1.

Table A-48 provides 48 compounds A-48.001 to A-48.048 of Formula (Ib), wherein A is N, $R^7$ is —$C(O)_2CH_2CH_3$, $R^1$ is tetrahydrofuran-2-yl, $R^2$ is fluoro, and $R^4$, $R^5$, $R^6$ and $R^8$ are as defined in Table 1.

Table A-49 provides 48 compounds A-49.001 to A-49.048 of Formula (Ib), wherein A is N, $R^7$ is —$C(O)_2CH_2CH_3$, $R^1$ is oxetane-3-yl, $R^2$ is hydrogen, and $R^4$, $R^5$, $R^6$ and $R^8$ are as defined in Table 1.

Table A-50 provides 48 compounds A-50.001 to A-50.048 of Formula (Ib), wherein A is N, $R^7$ is —$C(O)_2CH_2CH_3$, $R^1$ is oxetane-3-yl, $R^2$ is fluoro, and $R^4$, $R^5$, $R^6$ and $R^8$ are as defined in Table 1.

Table A-51 provides 48 compounds A-51.001 to A-51.048 of Formula (Ib), wherein A is N, $R^7$ is —$C(O)_2CH_2CH_3$, $R^1$ is 1-methylsulfonylethyl, $R^2$ is hydrogen, and $R^4$, $R^5$, $R^6$ and $R^8$ are as defined in Table 1.

Table A-52 provides 48 compounds A-52.001 to A-52.048 of Formula (Ib), wherein A is N, $R^7$ is —$C(O)_2CH_2CH_3$, $R^1$ is 1-methylsulfonylethyl, $R^2$ is fluoro, and $R^4$, $R^5$, $R^6$ and $R^8$ are as defined in Table 1.

Table A-53 provides 48 compounds A-53.001 to A-53.048 of Formula (Ib), wherein A is N, $R^7$ is —$C(O)_2CH_2CH_3$, $R^1$ is 1-methylsulfinylethyl, $R^2$ is hydrogen, and $R^4$, $R^5$, $R^6$ and $R^8$ are as defined in Table 1.

Table A-54 provides 48 compounds A-54.001 to A-54.048 of Formula (Ib), wherein A is N, $R^7$ is —$C(O)_2CH_2CH_3$, $R^1$ is 1-methylsulfinylethyl, $R^2$ is fluoro, and $R^4$, $R^5$, $R^6$ and $R^8$ are as defined in Table 1.

Table A-55 provides 48 compounds A-55.001 to A-55.048 of Formula (Ib), wherein A is N, $R^7$ is —$C(O)_2CH_2CH_3$, $R^1$ is 1-methylsulfanylethyl, $R^2$ is hydrogen, and $R^4$, $R^5$, $R^6$ and $R^8$ are as defined in Table 1.

Table A-56 provides 48 compounds A-56.001 to A-56.048 of Formula (Ib), wherein A is N, $R^7$ is —$C(O)_2CH_2CH_3$, $R^1$ is 1-methylsulfanylethyl, $R^2$ is fluoro, and $R^4$, $R^5$, $R^6$ and $R^8$ are as defined in Table 1.

Table A-57 provides 48 compounds A-57.001 to A-57.048 of Formula (Ib), wherein A is N, $R^7$ is —$C(O)_2CH_2CH_3$, $R^1$ is 1-methoxyethyl, $R^2$ is hydrogen, and $R^4$, $R^5$, $R^6$ and $R^8$ are as defined in Table 1.

Table A-58 provides 48 compounds A-58.001 to A-58.048 of Formula (Ib), wherein A is N, $R^7$ is —$C(O)_2CH_2CH_3$, $R^1$ is 1-methoxyethyl, $R^2$ is fluoro, and $R^4$, $R^5$, $R^6$ and $R^3$ are as defined in Table 1.

Table A-59 provides 48 compounds A-59.001 to A-59.048 of Formula (Ib), wherein A is N, $R^7$ is —$C(O)_2CH_2CH_3$, $R^1$ is 1-isopropoxyethyl, $R^2$ is hydrogen, and $R^4$, $R^5$, $R^6$ and $R^8$ are as defined in Table 1.

Table A-60 provides 48 compounds A-60.001 to A-60.048 of Formula (Ib), wherein A is N, $R^7$ is —$C(O)_2CH_2CH_3$, $R^1$ is 1-isopropoxyethyl, $R^2$ is fluoro, and $R^4$, $R^5$, $R^6$ and $R^8$ are as defined in Table 1.

Table A-61 provides 48 compounds A-61.001 to A-61.048 of Formula (Ib), wherein A is N, $R^7$ is —$C(O)_2CH_2CH_3$, $R^1$ is 1-tert-butoxyethyl, $R^2$ is hydrogen, and $R^4$, $R^5$, $R^6$ and $R^8$ are as defined in Table 1.

Table A-62 provides 48 compounds A-62.001 to A-62.048 of Formula (Ib), wherein A is N, $R^7$ is —$C(O)_2CH_2CH_3$, $R^1$ is 1-tert-butoxyethyl, $R^2$ is fluoro, and $R^4$, $R^5$, $R^6$ and $R^3$ are as defined in Table 1.

Table A-63 provides 48 compounds A-63.001 to A-63.048 of Formula (Ib), wherein A is N, $R^7$ is —$C(O)_2CH_2CH_3$, $R^1$ is isopropoxymethyl, $R^2$ is hydrogen, and $R^4$, $R^5$, $R^6$ and $R^3$ are as defined in Table 1.

Table A-64 provides 48 compounds A-64.001 to A-64.048 of Formula (Ib), wherein A is N, $R^7$ is —$C(O)_2CH_2CH_3$, $R^1$ is isopropoxymethyl, $R^2$ is fluoro, and $R^4$, $R^5$, $R^6$ and $R^8$ are as defined in Table 1.

Table A-65 provides 48 compounds A-65.001 to A-65.048 of Formula (Ib), wherein A is N, $R^7$ is —$C(O)_2CH_2CH_3$, $R^1$ is tert-butoxymethyl, $R^2$ is hydrogen, and $R^4$, $R^5$, $R^6$ and $R^8$ are as defined in Table 1.

Table A-66 provides 48 compounds A-66.001 to A-66.048 of Formula (Ib), wherein A is N, $R^7$ is —$C(O)_2CH_2CH_3$, $R^1$ is tert-butoxymethyl, $R^2$ is fluoro, and $R^4$, $R^5$, $R^6$ and $R^8$ are as defined in Table 1.

Table A-67 provides 12 compounds A-67.001 to A-66.012 of Formula (Ib), wherein A is N, $R^7$ is hydrogen, $R^1$ is tetrahydropyran-4-yl, $R^2$ is hydrogen, and $R^4$, $R^5$, $R^6$ and $R^8$ are as defined in Table 1.

Table A-68 provides 12 compounds A-68.001 to A-68.012 of Formula (Ib), wherein A is N, $R^7$ is hydrogen, $R^1$ is tetrahydropyran-4-yl, $R^2$ is fluoro, and $R^4$, $R^5$, $R^6$ and $R^8$ are as defined in Table 1.

Formulation Examples

| Wettable powders | a) | b) | c) |
|---|---|---|---|
| active ingredient [compound of formula (I)] | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| phenol polyethylene glycol ether (7-8 mol of ethylene oxide) | — | 2% | — |

-continued

| Wettable powders | a) | b) | c) |
|---|---|---|---|
| highly dispersed silicic acid | 5% | 10% | 10% |
| Kaolin | 62% | 27% | — |

The active ingredient is thoroughly mixed with the adjuvants and the mixture is thoroughly ground in a suitable mill, affording wettable powders that can be diluted with water to give suspensions of the desired concentration.

| Powders for dry seed treatment | a) | b) | c) |
|---|---|---|---|
| active ingredient [compound of formula (I)] | 25% | 50% | 75% |
| light mineral oil | 5% | 5% | 5% |
| highly dispersed silicic acid | 5% | 5% | — |
| Kaolin | 65% | 40% | — |
| Talcum | — | | 20% |

The active ingredient is thoroughly mixed with the adjuvants and the mixture is thoroughly ground in a suitable mill, affording powders that can be used directly for seed treatment.

| Emulsifiable concentrate | |
|---|---|
| active ingredient [compound of formula (I)] | 10% |
| octylphenol polyethylene glycol ether (4-5 mol of ethylene oxide) | 3% |
| calcium dodecylbenzenesulfonate | 3% |
| castor oil polyglycol ether (35 mol of ethylene oxide) | 4% |
| Cyclohexanone | 30% |
| xylene mixture | 50% |

Emulsions of any required dilution, which can be used in plant protection, can be obtained from this concentrate by dilution with water.

| Dusts | a) | b) | c) |
|---|---|---|---|
| Active ingredient [compound of formula (I)] | 5% | 6% | 4% |
| talcum | 95% | — | — |
| Kaolin | — | 94% | — |
| mineral filler | — | — | 96% |

Ready-for-use dusts are obtained by mixing the active ingredient with the carrier and grinding the mixture in a suitable mill. Such powders can also be used for dry dressings for seed.

| Extruder granules | |
|---|---|
| Active ingredient [compound of formula (I)] | 15% |
| sodium lignosulfonate | 2% |
| carboxymethylcellulose | 1% |
| Kaolin | 82% |

The active ingredient is mixed and ground with the adjuvants, and the mixture is moistened with water. The mixture is extruded and then dried in a stream of air.

| Coated granules | |
|---|---|
| Active ingredient [compound of formula (I)] | 8% |
| polyethylene glycol (mol. wt. 200) | 3% |
| Kaolin | 89% |

The finely ground active ingredient is uniformly applied, in a mixer, to the kaolin moistened with polyethylene glycol. Non-dusty coated granules are obtained in this manner.

| Suspension concentrate | |
|---|---|
| active ingredient [compound of formula (I)] | 40% |
| propylene glycol | 10% |
| nonylphenol polyethylene glycol ether (15 mol of ethylene oxide) | 6% |
| Sodium lignosulfonate | 10% |
| carboxymethylcellulose | 1% |
| silicone oil (in the form of a 75% emulsion in water) | 1% |
| Water | 32% |

The finely ground active ingredient is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

| Flowable concentrate for seed treatment | |
|---|---|
| active ingredient [compound of formula (I)] | 40% |
| propylene glycol | 5% |
| copolymer butanol PO/EO | 2% |
| tristyrenephenole with 10-20 moles EO | 2% |
| 1,2-benzisothiazolin-3-one (in the form of a 20% solution in water) | 0.5% |
| monoazo-pigment calcium salt | 5% |
| Silicone oil (in the form of a 75% emulsion in water) | 0.2% |
| Water | 45.3% |

The finely ground active ingredient is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

Slow Release Capsule Suspension 28 parts of a combination of the compound of formula (I) are mixed with 2 parts of an aromatic solvent and 7 parts of toluene diisocyanate/polymethylene-polyphenylisocyanate-mixture (8:1). This mixture is emulsified in a mixture of 1.2 parts of polyvinyl alcohol, 0.05 parts of a defoamer and 51.6 parts of water until the desired particle size is achieved. To this emulsion a mixture of 2.8 parts 1,6-diaminohexane in 5.3 parts of water is added. The mixture is agitated until the polymerization reaction is completed.

The obtained capsule suspension is stabilized by adding 0.25 parts of a thickener and 3 parts of a dispersing agent. The capsule suspension formulation contains 28% of the active ingredients. The medium capsule diameter is 8-15 microns.

The resulting formulation is applied to seeds as an aqueous suspension in an apparatus suitable for that purpose.

EXAMPLES

The Examples which follow serve to illustrate the invention. The compounds of the invention can be distinguished from known compounds by virtue of greater efficacy at low application rates, which can be verified by the person skilled in the art using the experimental procedures outlined in the Examples, using lower application rates if necessary, for example 50 ppm, 12.5 ppm, 6 ppm, 3 ppm, 1.5 ppm, 0.8 ppm or 0.2 ppm.

Compounds of formula (I) may possess any number of benefits including, interalia, advantageous levels of biological activity for protecting plants against diseases that are caused by fungi or superior properties for use as agrochemical active ingredients (for example, greater biological activity, an advantageous spectrum of activity, an increased safety profile (including improved crop tolerance), improved physico-chemical properties, or increased biodegradability).

List of Abbreviations

° C.=degrees Celsius, $CDCl_3$=chloroform-d, d=doublet, DCM=dichloromethane, DMF=dimethylformamide, HATU=1-[Bis(dimethylamino)methylene]-1H-1,2,3-triazolo[4,5-b]pyridinium 3-oxid hexafluorophosphate, m=multiplet, MHz=megahertz, N=normal, RT=room temperature, s=singlet General Throughout this description, temperatures are given in degrees Celsius (° C.) and "m.p." means melting point. LC/MS means Liquid Chromatography Mass Spectrometry and the description of the apparatus and the method is:

Method A: ACQUITY UPLC from Waters, Waters UPLC HSS T3, 1.8 mm particle size, 30×2.1 mm column, 0.85 mL/min., 60° C., H2O/MeOH 95:5+0.05% HCOOH (90%)/CH3CN+0.05% HCOOH (10%)-1.2 min.-CH3CN+0.05% HCOOH (100%)-0.30 min., ACQUITY SQD Mass Spectrometer from Waters, ionization method: electrospray (ESI), Polarity: positive ions, Capillary (kV) 3.00, Cone (V) 30.00, Extractor (V) 2.00, Source Temperature (° C.) 150, Desolvation Temperature (° C.) 350, Cone Gas Flow (L/Hr) 0, Desolvation Gas Flow (L/Hr) 650).

Method B: ACQUITY UPLC from Waters, Waters UPLC HSS T3, 1.8 mm particle size, 30×2.1 mm column, 0.85 mL/min., 60° C., H2O/MeOH 95:5+0.05% HCOOH (90%)/CH3CN+0.05% HCOOH (10%)-2.7 min.-CH3CN+0.05% HCOOH (100%)-0.30 min., ACQUITY SQD Mass Spectrometer from Waters, ionization method: electrospray (ESI), Polarity: positive ions, Capillary (kV) 3.00, Cone (V) 30.00, Extractor (V) 2.00, Source Temperature (° C.) 150, Desolvation Temperature (° C.) 350, Cone Gas Flow (L/Hr) 0, Desolvation Gas Flow (L/Hr) 650).

Method C: ACQUITY Mass Spectrometer from Waters Corporations (SQD or SQDII Single quadrupole mass spectrometer) equipped with an electrospray source (Polarity: positive or negative ions, Capillary: 3.0 kV, Cone: 30V, Extractor: 3.00 V, Source Temperature: 150° C., Desolvation Temperature: 400° C., Cone Gas Flow: 60 L/hr, Desolvation Gas Flow: 700 L/hr, Mass range: 140 to 800 Da) and an ACQUITY UPLC from Waters Corporations with solvent degasser, binary pump, heated column compartment and diode-array detector. Column: Waters UPLC HSS T3, 1.8 μm, 30×2.1 mm, Temp: 60° C., DAD Wavelength range (nm): 210 to 400, Solvent Gradient: A=Water/Methanol 9:1+0.1% formic acid, B=Acetonitrile+0.1% formic acid, gradient: 0-100% B in 2.5 min; Flow (ml/min) 0.75).

Example 1: Preparation of 2-[(2,6-difluoro-4-pyridyl)-(tetrahydrofuran-3-carbonyl)amino]-N-(2,2-dimethylcyclobutyl)-5-methyl-thiazole-4-carboxamide (Example P-2, Table 2) and 2-[(2,6-difluoro-4-pyridyl)-(tetrahydrofuran-3-carbonyl)amino]-N-(2,2-dimethylcyclobutyl)-5-methyl-N-(tetrahydrofuran-3-carbonyl)thiazole-4-carboxamide (Example P-1, Table 2)

(Compound P-3, Table 2)

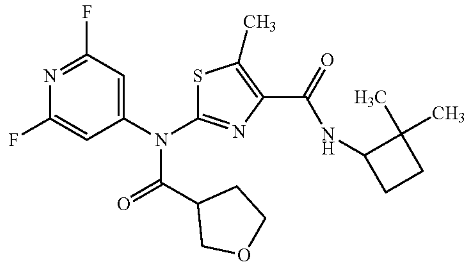

and (Compound P-1, Table 2)

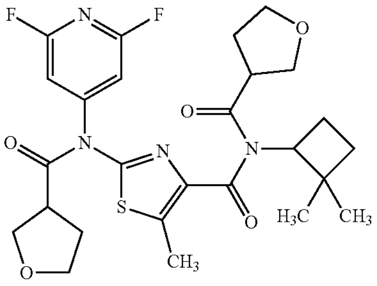

A solution of tetrahydrofuran-3-carboxylic acid (0.174 g, 0.143 mL, 1.48 mmol) in DCM (9 mL) under argon was treated with 1 drop of DMF, followed by oxalyl chloride (0.192 g, 0.13 mL, 1.48 mmol). The mixture was stirred for 30 minutes at RT under argon to give tetrahydrofuran-3-carbonyl chloride. To this DCM solution were added 2-[(2,6-difluoro-4-pyridyl)amino]-N-(2,2-dimethylcyclobutyl)-5-methyl-thiazole-4-carboxamide (0.350 g, 0.993 mmol, prepared as described in WO 2019/105933), followed by triethylamine (0.308 g, 0.42 mL, 2.98 mmol), under argon at RT. The resulting pale-yellow solution was stirred for 2.5 hours under argon at RT upon which time LCMS analysis showed reaction completion. The reaction mixture was treated with Isolute® and concentrated in vacuo. Purification by Flash chromatography eluting with ethyl acetate/cyclohexane gave a mixture of two products which was further purified by reverse phase chromatography to give as the first eluted product 2-[(2,6-difluoro-4-pyridyl)-(tetrahydrofuran-3-carbonyl)amino]-N-(2,2-dimethylcyclobutyl)-5-methyl-thiazole-4-carboxamide (Example P-2, Table 2) as a white powder.

$^1$H NMR (400 MHz, $CDCl_3$): δ ppm 0.94 (s, 3H) 1.13 (s, 3H) 1.49-1.59 (m, 2H) 1.65-1.78 (m, 1H) 1.95-2.15 (m, 1H) 2.19-2.30 (m, 1H) 2.30-2.40 (m, 1H) 2.81 (s, 3H) 2.99-3.14 (m, 1H) 3.80-3.88 (m, 1H) 3.88-3.95 (m, 1H) 3.95-4.06 (m, 2H) 4.10-4.26 (quadruplet, 1H) 6.89 (s, 2H) 6.95-7.06 (broad d, 1H);

LC-MS (Method A): 451 [M+H], Rt: 1.09 min.

Further elution gave the second product, 2-[(2,6-difluoro-4-pyridyl)-(tetrahydrofuran-3-carbonyl)amino]-N-(2,2-dimethylcyclobutyl)-5-methyl-N-(tetrahydrofuran-3-carbonyl)thiazole-4-carboxamide (Compound P-1, Table 2) as a white powder.

$^1$H NMR (400 MHz, $CDCl_3$): δ ppm 1.09 (s, 3H) 1.18 (s, 3H) 1.53-1.66 (m, 2H) 1.77-1.91 (m, 1H) 2.07-2.22 (m, 2H) 2.23-2.34 (m, 1H) 2.41-2.51+2.62-2.71 (2×m, 2H) 2.81 (s, 3H) 3.10-3.26 (m, 1H) 3.77-4.05 (m, 6H) 4.14-4.31+4.37-4.43 (2×m, 3H) 6.81-6.92 (2×s, 2H) 7.20 (br d, J=8.44 Hz, 1H);

LC-MS (Method A): 549 [M+H], Rt: 1.15 min.

Example 2: Preparation of 2-[(2,6-difluoro-4-pyridyl)-(oxetane-3-carbonyl)amino]-N-(2,2-dimethylcyclobutyl)-5-methyl-thiazole-4-carboxamide (Example P-4, Table 2)

(Example P-4, Table 2)

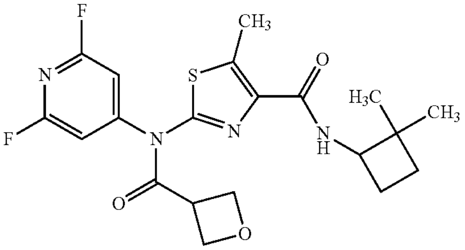

A solution of 2-[(2,6-difluoro-4-pyridyl)amino]-N-(2,2-dimethylcyclobutyl)-5-methyl-thiazole-4-carboxamide (0.050 g, 1.0, 0.14 mmol, prepared as described in WO 2019/105933) in DMF (1.4 mL) was treated with oxetane-3-carboxylic acid (0.019 g, 1.2, 0.17 mmol), N,N-diisopropylethylamine (0.048 g, 0.064 mL, 0.37 mmol), and HATU (0.082 g, 0.21 mmol). The resulting pale brown solution was stirred for 4 hours at RT. After this time, the reaction mixture was quenched with saturated aqueous sodium bicarbonate and diluted with water. It was then extracted twice with ethyl acetate and the combined organic layers were washed with brine, dried over anhydrous $Na_2SO_4$, filtered and concentrated in vacuo to give a pale brown oil. The crude product was purified by reversed phase chromatography eluting with acetonitrile/water to give the title compound as a beige powder.

$^1$H NMR (400 MHz, $CDCl_3$) δ ppm 0.97 (s, 3H) 1.14 (s, 3H) 1.50-1.65 (m, 2H) 1.65-1.81 (m, 1H) 2.19-2.34 (m, 1H) 2.84 (s, 3H) 3.86-4.01 (m, 1H) 4.13-4.26 (m, 1H) 4.51-4.65 (m, 2H) 4.92-5.06 (m, 2H) 6.82 (s, 2H) 6.91-7.08 (br s, 1H); LC-MS (Method A): 437 [M+H], Rt: 1.05 min.

Example 3: Preparation of 2-[(2,6-difluoro-4-pyridyl)-(tetrahydropyran-4-carbonyl)amino]-N-(2,2-dimethylcyclobutyl)-5-methyl-thiazole-4-carboxamide (Example P-11, Table 2)

A solution of tetrahydro-2h-pyran-4-carboxylic acid (6.282 g, 46.82 mmol) in acetonitrile (86 mL) was treated with 1-propanephosphonic anhydride (99.32 g, 93.00 mL, 156.1 mmol), N,N-diisopropylethylamine (40.75 g, 54.6 mL, 10.00, 312.1 mmol) and 2-[(2,6-difluoro-4-pyridyl)amino]-N-(2,2-dimethylcyclobutyl)-5-methyl-thiazole-4-carboxamide (11 g, 1.000, 31.21 mmol, prepared as described in WO 2019/105933) were added to give a brown solution. The reaction mixture was stirred for 16 Hr at 50° C. under argon. After reaction completion, the reaction mixture was allowed to cool and slowly added to aqueous saturated sodium bicarbonate solution at 0° C. The reaction mixture was then extracted with ethyl acetate (×3) and the combined organic extracts washed once with brine, dried over anhydrous $Na_2SO_4$, filtered and concentrated in vacuo to give 15.88 g of a pale brown powder. Flash chromatography eluting with an ethyl acetate/cyclohexane gave the title product as a white powder. $^1H$ NMR (400 MHz, $CDCl_3$) δ ppm 0.93 (s, 3H) 1.13 (s, 3H) 1.50-1.76 (m, 5H) 1.97-2.09 (m, 2H) 2.25 (dtd, J=10.90, 8.08, 8.08, 2.72 Hz, 1H) 2.60 (tt, J=11.26, 3.81 Hz, 1H) 2.81 (s, 3H) 3.29 (tt, J=11.90, 1.91 Hz, 2H) 4.01 (dt, J=11.63, 2.18 Hz, 2H) 4.18 (q, J=8.60 Hz, 1H) 6.89 (s, 2H) 6.99 (br d, J=9.08 Hz, 1H)

LC-MS (Method A): 465 [M+H], Rt: 1.11 min.

Table 2 below illustrates exemplified individual compounds of formula (I) according to the invention.

TABLE 2

Melting point and LC/MS data ($R_t$ = Retention time) for selected compounds of Table 1.

| No. | Compound Name | Structure | Mp (° C.) | LC/MS |
|---|---|---|---|---|
| P-1 | 2-[(2,6-difluoro-4-pyridyl)-(tetrahydrofuran-3-carbonyl)amino]-N-(2,2-dimethylcyclobutyl)-5-methyl-N-(tetrahydrofuran-3-carbonyl)thiazole-4-carboxamide | 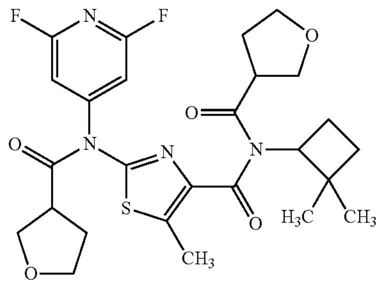 [SMILES: Cc1sc(N(C(=O)C2CCOC2)c2cc(F)nc(F)c2)nc1C(=O)N(C(=O)C1CCOC1)C1CCC1(C)C] | | $R_t$ = 1.15 min (A); MS: m/z = 549 (M + 1) |
| P-2 | 2-[(2,6-difluoro-4-pyridyl)-(tetrahydrofuran-2-carbonyl)amino]-N-(2,2-dimethylcyclobutyl)-5-methyl-thiazole-4-carboxamide | 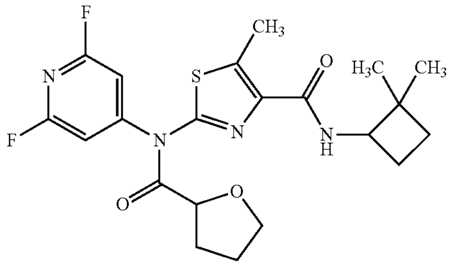 [SMILES: Cc1sc(N(C(=O)C2CCCO2)c2cc(F)nc(F)c2)nc1C(=O)NC1CCC1(C)C] | | $R_t$ = 1.13 min (A); MS: m/z = 451 (M + 1) |
| P-3 | 2-[(2,6-difluoro-4-pyridyl)-(tetrahydrofuran-3-carbonyl)amino]-N-(2,2-dimethylcyclobutyl)-5-methyl-thiazole-4-carboxamide | 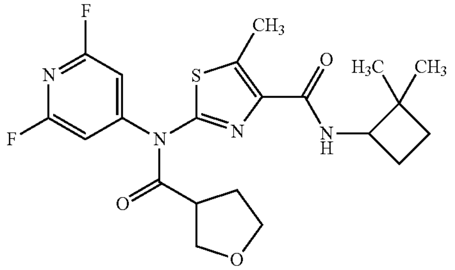 [SMILES: Cc1sc(N(C(=O)C2CCOC2)c2cc(F)nc(F)c2)nc1C(=O)NC1CCC1(C)C] | | $R_t$ = 1.09 min (A); MS: m/z = 451 (M + 1) |
| P-4 | 2-[(2,6-difluoro-4-pyridyl)-(oxetane-3-carbonyl)amino]-N-(2,2-dimethylcyclobutyl)-5-methyl-thiazole-4-carboxamide | 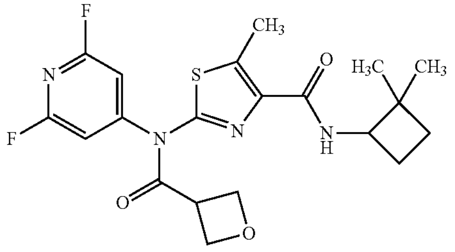 [SMILES: Cc1sc(N(C(=O)C2COC2)c2cc(F)nc(F)c2)nc1C(=O)NC1CCC1(C)C] | | $R_t$ = 1.05 min (A); MS: m/z = 437 (M + 1) |

TABLE 2-continued

| Melting point and LC/MS data ($R_t$ = Retention time) for selected compounds of Table 1. | | | | |
|---|---|---|---|---|
| No. | Compound Name | Structure | Mp (° C.) | LC/MS |
| P-5 | 2-[2-tert-butoxypropanoyl-(2,6-difluoro-4-pyridyl)amino]-N-(2,2-dimethylcyclobutyl)-5-methyl-thiazole-4-carboxamide | 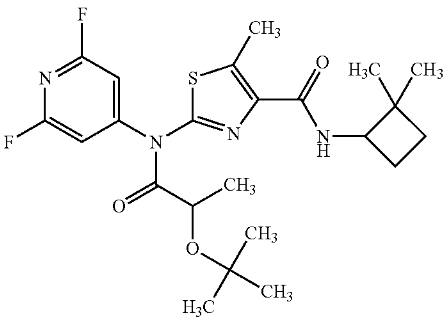 [SMILES: Cc1sc(N(C(=O)C(C)OC(C)(C)C)c2cc(F)nc(F)c2)nc1C(=O)NC1CCC1(C)C] | 107-112 | $R_t$ = 1.22 min (A); MS: m/z = 481 (M + 1) |
| P-6 | 2-[(2,6-difluoro-4-pyridyl)-(2-isopropoxypropanoyl)amino]-N-(2,2-dimethylcyclobutyl)-5-methyl-thiazole-4-carboxamide | 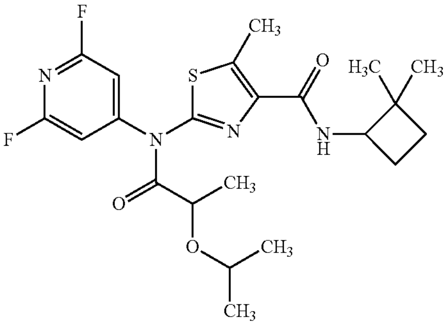 [SMILES: Cc1sc(N(C(=O)C(C)OC(C)C)c2cc(F)nc(F)c2)nc1C(=O)NC1CCC1(C)C] | | $R_t$ = 1.20 min (A); MS: m/z = 467 (M + 1) |
| P-7 | 2-[(2-tert-butoxyacetyl)-(2,6-difluoro-4-pyridyl)amino]-N-(2,2-dimethylcyclobutyl)-5-methyl-thiazole-4-carboxamide | 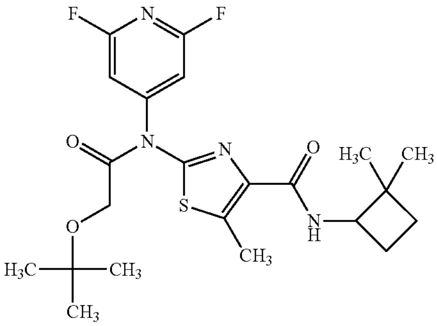 [SMILES: Cc1sc(N(C(=O)COC(C)(C)C)c2cc(F)nc(F)c2)nc1C(=O)NC1CCC1(C)C] | 159-161 | $R_t$ = 1.20 min (A); MS: m/z = 467 (M + 1) |
| P-8 | 2-[(2,6-difluoro-4-pyridyl)-(2-isopropoxyacetyl)amino]-N-(2,2-dimethylcyclobutyl)-5-methyl-thiazole-4-carboxamide | 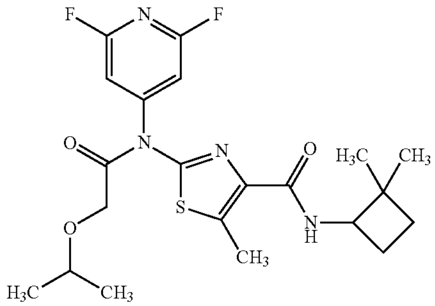 [SMILES: Cc1sc(N(C(=O)COC(C)C)c2cc(F)nc(F)c2)nc1C(=O)NC1CCC1(C)C] | 170-172 | $R_t$ = 1.16 min (A); MS: m/z = 453 (M + 1) |

TABLE 2-continued

Melting point and LC/MS data ($R_t$ = Retention time) for selected compounds of Table 1.

| No. | Compound Name | Structure | Mp (° C.) | LC/MS |
|---|---|---|---|---|
| P-9 | 2-[(2,6-difluoro-4-pyridyl)-(2-methoxypropanoyl)amino]-N-(2,2-dimethylcyclobutyl)-5-methyl-thiazole-4-carboxamide | 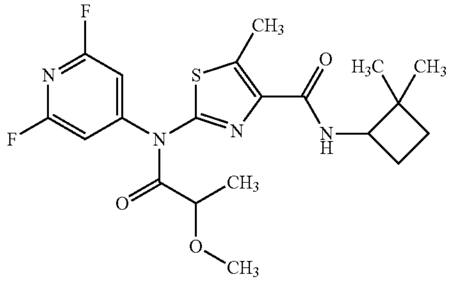 [SMILES: COC(C)C(=O)N(c1cc(F)nc(F)c1)c1nc(C(=O)NC2CCC2(C)C)c(C)s1] | | $R_t$ = 1.12 min (A); MS: m/z = 439 (M + 1) |
| P-10 | 2-[(2,6-difluoro-4-pyridyl)-(2-methylsulfonylpropanoyl)amino]-N-(2,2-dimethylcyclobutyl)-5-methyl-thiazole-4-carboxamide | 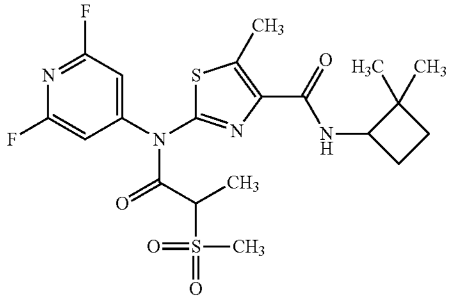 [SMILES: Cc1sc(N(C(=O)C(C)S(C)(=O)=O)c2cc(F)nc(F)c2)nc1C(=O)NC1CCC1(C)C] | | $R_t$ = 1.02 min (A); MS: m/z = 487 (M + 1) |
| P-11 | 2-[(2,6-difluoro-4-pyridyl)-(tetrahydropyran-4-carbonyl)amino]-N-(2,2-dimethylcyclobutyl)-5-methyl-thiazole-4-carboxamide | 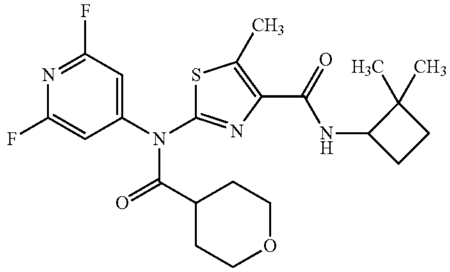 [SMILES: Cc1sc(N(C(=O)C2CCOCC2)c2cc(F)nc(F)c2)nc1C(=O)NC1CCC1(C)C] | | $R_t$ = 1.11 min (A); MS: m/z = 465 (M + 1) |

Biological Examples

Example B1: *Alternaria solani*/Tomato/Leaf Disc (Early Blight)

Tomato leaf disks cv. Baby are placed on agar in multiwell plates (24-well format) and sprayed with the formulated test compound diluted in water. The leaf disks are inoculated with a spore suspension of the fungus 2 days after application. The inoculated leaf disks are incubated at 23° C./21° C. (day/night) and 80% rh under a light regime of 12/12 h (light/dark) in a climate cabinet and the activity of a compound is assessed as percent disease control compared to untreated when an appropriate level of disease damage appears on untreated check disk leaf disks (5-7 days after application). The following compounds gave at least 80% control of *Alternaria solani* at 200 ppm when compared to untreated control under the same conditions, which showed extensive disease development: P-1, P-2, P-3, P-4, P-5, P-6, P-9, P-10, and P-11.

Example B2: *Botryotinia Fuckeliana* (*Botrytis cinerea*)/Liquid Culture (Gray Mould)

Conidia of the fungus from cryogenic storage are directly mixed into nutrient broth (Vogels broth). After placing a (DMSO) solution of test compound into a microtiter plate (96-well format), the nutrient broth containing the fungal spores is added. The test plates are incubated at 24° C. and the inhibition of growth is determined photometrically 3-4 days after application. The following compounds gave at least 80% control of *Botryotinia fuckeliana* at 20 ppm when compared to untreated control under the same conditions, which showed extensive disease development: P-2, and P-4.

Example B3: *Glomerella Lagenarium* (*Colletotrichum Lagenarium*)/Liquid Culture (Anthracnose)

Conidia of the fungus from cryogenic storage are directly mixed into nutrient broth (PDB potato dextrose broth). After placing a (DMSO) solution of test compound into a microtiter plate (96-well format), the nutrient broth containing the fungal spores is added. The test plates are incubated at 24° C. and the inhibition of growth is measured photometrically 3-4 days after application. The following compounds gave at least 80% control of *Glomerella lagenarium* at 20 ppm when compared to untreated control under the same conditions, which showed extensive disease development: P-1, P-2, P-3, P-4, P-6, P-9, P-10, and P-11.

Example B4: *Blumeria graminis* f. Sp. *Tritici* (*Erysiphe graminis* f. Sp. *Tritici*)/Wheat/Leaf Disc Preventative (Powdery Mildew on Wheat)

Wheat leaf segments cv. Kanzler are placed on agar in a multiwell plate (24-well format) and sprayed with the formulated test compound diluted in water. The leaf disks are inoculated by shaking powdery mildew infected plants above the test plates 1 day after application. The inoculated leaf disks are incubated at 20° C. and 60% rh under a light regime of 24 h darkness followed by 12 h light/12 h darkness in a climate chamber and the activity of a compound is assessed as percent disease control compared to untreated when an appropriate level of disease damage appears on untreated check leaf segments (6-8 days after application). The following compounds gave at least 80% control of *Blumeria graminis* f. sp. *tritici* at 200 ppm when compared to untreated control under the same conditions, which showed extensive disease development: P-1, P-2, P-3, P-4, P-5, P-6, P-7, P-8, P-9, P-10, and P-11.

Example B5: *Phaeosphaeria Nodorum* (*Septoria nodorum*)/Wheat/Leaf Disc Preventative (Glume Blotch)

Wheat leaf segments cv. Kanzler are placed on agar in a multiwell plate (24-well format) and sprayed with the formulated test compound diluted in water. The leaf disks are inoculated with a spore suspension of the fungus 2 days after application. The inoculated test leaf disks are incubated at 20° C. and 75% rh under a light regime of 12 h light/12 h darkness in a climate cabinet and the activity of a compound is assessed as percent disease control compared to untreated when an appropriate level of disease damage appears in untreated check leaf disks (5-7 days after application). The following compounds gave at least 80% control of *Phaeosphaeria nodorum* at 200 ppm when compared to untreated control under the same conditions, which showed extensive disease development: P-2, P-3, and P-10.

Example B6: *Monographella Nivalis* (*Microdochium Nivale*)/Liquid Culture (Foot Rot Cereals)

Conidia of the fungus from cryogenic storage are directly mixed into nutrient broth (PDB potato dextrose broth). After placing a (DMSO) solution of test compound into a microtiter plate (96-well format), the nutrient broth containing the fungal spores is added. The test plates are incubated at 24° C. and the inhibition of growth is determined photometrically 4-5 days after application. The following compounds gave at least 80% control of *Monographella nivalis* at 20 ppm when compared to untreated control under the same conditions, which showed extensive disease development: P-1, P-2, P-3, P-4, P-5, P-6, P-9, P-10, and P-11.

Example B7: *Mycosphaerella arachidis* (*Cercospora arachidicola*)/Liquid Culture (Early Leaf Spot)

Conidia of the fungus from cryogenic storage are directly mixed into nutrient broth (PDB potato dextrose broth). After placing a (DMSO) solution of test compound into a microtiter plate (96-well format), the nutrient broth containing the fungal spores is added. The test plates are incubated at 24° C. and the inhibition of growth is determined photometrically 4-5 days after application. The following compounds gave at least 80% control of *Mycosphaerella arachidis* at 20 ppm when compared to untreated control under the same conditions, which showed extensive disease development: P-1, P-2, and P-10.

Example B8: *Phakopsora pachyrhizi*/Soybean/Preventative (Soybean Rust)

Soybean leaf disks are placed on water agar in multiwell plates (24-well format) and sprayed with the formulated test compound diluted in water. One day after application leaf discs are inoculated by spraying a spore suspension on the lower leaf surface. After an incubation period in a climate cabinet of 24-36 hours in darkness at 20° C. and 75% rh leaf disc are kept at 20° C. with 12 h light/day and 75% rh. The activity of a compound is assessed as percent disease control compared to untreated when an appropriate level of disease damage appears in untreated check leaf disks (12-14 days after application). The following compounds gave at least 80% control of *Phakopsora pachyrhizi* at 200 ppm when compared to untreated control under the same conditions, which showed extensive disease development: P-2, P-3, P-4, P-6, and P-9.

Example B9: *Puccinia recondita* f. Sp. *Tritici*/Wheat/Leaf Disc Curative (Brown Rust)

Wheat leaf segments cv. Kanzler are placed on agar in multiwell plates (24-well format). The leaf segments are inoculated with a spore suspension of the fungus. Plates are stored in darkness at 19° C. and 75% rh. The formulated test compound diluted in water is applied 1 day after inoculation. The leaf segments are incubated at 19° C. and 75% rh under a light regime of 12 h light/12 h darkness in a climate cabinet and the activity of a compound is assessed as percent disease control compared to untreated when an appropriate level of disease damage appears in untreated check leaf segments (6-8 days after application). The following compounds gave at least 80% control of *Puccinia recondita* f. sp. *tritici* at 200 ppm when compared to untreated control under the same conditions, which showed extensive disease development: P-1, P-2, P-3, P-4, P-5, P-6, P-9, and P-11.

Example B10: *Puccinia recondita* f. Sp. *Tritici*/Wheat/Leaf Disc Preventative (Brown Rust)

Wheat leaf segments cv. Kanzler are placed on agar in multiwell plates (24-well format) and sprayed with the formulated test compound diluted in water. The leaf disks are inoculated with a spore suspension of the fungus 1 day after application. The inoculated leaf segments are incubated at 19° C. and 75% rh under a light regime of 12 h light/12 h darkness in a climate cabinet and the activity of a compound is assessed as percent disease control compared to untreated when an appropriate level of disease damage appears in untreated check leaf segments (7-9 days after application). The following compounds gave at least 80% control of *Puccinia recondita* f. sp. *tritici* at 200 ppm when compared to untreated control under the same conditions, which showed extensive disease development: P-1, P-2, P-3, P-4, P-5, P-6, P-7, P-9, P-10, and P-11.

Example B11: *Magnaporthe grisea* (*Pyricularia oryzae*)/Rice/Leaf Disc Preventative (Rice Blast)

Rice leaf segments cv. Ballila are placed on agar in a multiwell plate (24-well format) and sprayed with the formulated test compound diluted in water. The leaf segments are inoculated with a spore suspension of the fungus 2 days after application. The inoculated leaf segments are incubated at 22° C. and 80% rh under a light regime of 24 h darkness followed by 12 h light/12 h darkness in a climate cabinet and the activity of a compound is assessed as percent disease control compared to untreated when an appropriate level of disease damage appears in untreated check leaf segments (5-7 days after application). The following compounds gave at least 80% control of *Magnaporthe grisea* at 200 ppm when compared to untreated control under the same conditions, which showed extensive disease development: P-1, P-2, P-3, P-4, P-5, P-6, P-7, P-8, P-9, and P-10.

Example B12: *Pyrenophora teres*/Barley/Leaf Disc Preventative (Net Blotch)

Barley leaf segments cv. Hasso are placed on agar in a multiwell plate (24-well format) and sprayed with the formulated test compound diluted in water. The leaf segmens are inoculated with a spore suspension of the fungus 2 days after application. The inoculated leaf segments are incubated at 20° C. and 65% rh under a light regime of 12 h light/12 h darkness in a climate cabinet and the activity of a compound is assessed as disease control compared to untreated when an appropriate level of disease damage appears in untreated check leaf segments (5-7 days after application). The following compounds gave at least 80% control of *Pyrenophora teres* at 200 ppm when compared to untreated control under the same conditions, which showed extensive disease development: P-1, P-2, P-3, P-4, P-5, P-6, P-9, P-10, and P-11.

Example B13: *Sclerotinia scierotiorum*/Liquid Culture (Cottony Rot)

Mycelia fragments of a newly grown liquid culture of the fungus are directly mixed into nutrient broth (PDB potato dextrose broth). After placing a (DMSO) solution of test compound into a microtiter plate (96-well format) the nutrient broth containing the fungal material is added. The test plates are incubated at 24° C. and the inhibition of growth is determined photometrically 3-4 days after application. The following compounds gave at least 80% control of *Sclerotinia sclerotiorum* at 20 ppm when compared to untreated control under the same conditions, which showed extensive disease development: P-10.

Example B14: *Mycosphaerella graminicola* (*Septoria tritici*)/Liquid Culture (*Septoria* Blotch)

Conidia of the fungus from cryogenic storage are directly mixed into nutrient broth (PDB potato dextrose broth). After placing a (DMSO) solution of test compound into a microtiter plate (96-well format), the nutrient broth containing the fungal spores is added. The test plates are incubated at 24° C. and the inhibition of growth is determined photometrically 4-5 days after application. The following compounds gave at least 80% control of *Mycosphaerella graminicola* at 20 ppm when compared to untreated control under the same conditions, which showed extensive disease development: P-1, P-2, P-3, P-4, P-9, P-10, and P-11.

The invention claimed is:

1. A compound of Formula (I):

(I)

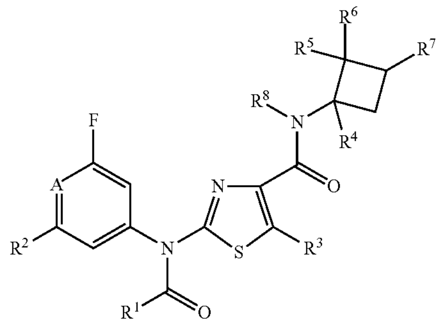

wherein

A is N;

$R^1$ is oxetane-3-yl, tetrahydrofuran-2-yl, tetrahydrofuran-3-yl, or tetrahydropyran-4-yl;

$R^2$ is hydrogen or halogen;

$R^3$ is $C_1$-$C_3$alkyl;

$R^4$ is hydrogen;

$R^5$, $R^6$ are each independently $C_1$-$C_4$alkyl;

$R^7$ is hydrogen, $C_1$-$C_4$alkyl, $C_1$-$C_6$alkoxycarbonyl$C_1$-$C_4$alkyl, $C_1$-$C_6$alkoxycarbonyl, or $C_1$-$C_6$alkoxy;

$R^8$ is hydrogen, $C_1$-$C_6$alkoxy$C_1$-$C_6$alkycarbonyl, $C_1$-$C_6$alkylsulfanyl$C_1$-$C_6$alkylcarbonyl, $C_1$-$C_6$alkylsulfinyl$C_1$-$C_6$alkycarbonyl, $C_1$-$C_6$alkylsulfonyl$C_1$-$C_6$alkycarbonyl, or heterocyclylcarbonyl, wherein the heterocyclyl moiety is a 4-, 5- or 6-membered non-aromatic monocyclic ring comprising 1, 2 or 3 heteroatoms individually selected from nitrogen, oxygen and sulfur;

or a salt or an N-oxide thereof.

2. The compound according to claim 1, wherein $R^2$ is fluoro.

3. The compound according to claim 1, wherein $R^3$ is methyl.

4. The compound according to claim 1, wherein $R^5$ and $R^6$ are both methyl.

5. An agrochemical composition comprising a fungicidally effective amount of a compound of formula (I) according to claim 1.

6. The composition according to claim 5, further comprising at least one additional active ingredient and/or an agrochemically-acceptable diluent or carrier.

7. A method of controlling or preventing infestation of useful plants by phytopathogenic fungi, the method comprises applying to the useful plants, to parts thereof or the locus thereof a fungicidally effective amount of the compound of formula (I) according to claim 1.

8. The compound according to claim 1, selected from

2-[(2,6-difluoro-4-pyridyl)-(tetrahydrofuran-3-carbonyl)amino]-N-(2,2-dimethylcyclobutyl)-5-methyl-N-(tetrahydrofuran-3-carbonyl)thiazole-4-carboxamide;

2-[(2,6-difluoro-4-pyridyl)-(tetrahydrofuran-2-carbonyl)amino]-N-(2,2-dimethylcyclobutyl)-5-methyl-thiazole-4-carboxamide;

2-[(2,6-difluoro-4-pyridyl)-(tetrahydrofuran-3-carbonyl)amino]-N-(2,2-dimethylcyclobutyl)-5-methyl-thiazole-4-carboxamide;

2-[(2,6-difluoro-4-pyridyl)-(oxetane-3-carbonyl)amino]-N-(2,2-dimethylcyclobutyl)-5-methyl-thiazole-4-carboxamide; and 2-[(2,6-difluoro-4-pyridyl)-(tetrahydropyran-4-carbonyl)amino]-N-(2,2-dimethylcyclobutyl)-5-methyl-thiazole-4-carboxamide.

9. The compound according to claim 1, selected from:

2-[(2,6-difluoro-4-pyridyl)-(tetrahydrofuran-2-carbonyl)amino]-N-(2,2-dimethylcyclobutyl)-5-methyl-thiazole-4-carboxamide;

2-[(2,6-difluoro-4-pyridyl)-(tetrahydrofuran-3-carbonyl)amino]-N-(2,2-dimethylcyclobutyl)-5-methyl-thiazole-4-carboxamide;

2-[(2,6-difluoro-4-pyridyl)-(oxetane-3-carbonyl)amino]-N-(2,2-dimethylcyclobutyl)-5-methyl-thiazole-4-carboxamide; and 2-[(2,6-difluoro-4-pyridyl)-(tetrahydropyran-4-carbonyl)amino]-N-(2,2-dimethylcyclobutyl)-5-methyl-thiazole-4-carboxamide.

10. The compound according to claim 1, selected from:

2-[(2,6-difluoro-4-pyridyl)-(tetrahydrofuran-2-carbonyl)amino]-N-(2,2-dimethylcyclobutyl)-5-methyl-thiazole-4-carboxamide; and 2-[(2,6-difluoro-4-pyridyl)-(tetrahydrofuran-3-carbonyl)amino]-N-(2,2-dimethylcyclobutyl)-5-methyl-thiazole-4-carboxamide.

11. An agrochemical composition comprising a fungicidally effective amount of the compound according to claim 8.

12. A method of controlling or preventing infestation of useful plants by phytopathogenic fungi, the method comprising applying to the useful plants, to parts thereof or the locus thereof a fungicidally effective amount of the compound according to claim 8.

* * * * *